(12) United States Patent
Ye et al.

(10) Patent No.: US 11,396,504 B2
(45) Date of Patent: Jul. 26, 2022

(54) ALKOXYBENZO-FIVE-MEMBERED (SIX-MEMBERED) HETEROCYCLIC AMINE COMPOUND AND PHARMACEUTICAL USE THEREOF

(71) Applicant: FUDAN UNIVERSITY, Shanghai (CN)

(72) Inventors: Deyong Ye, Shanghai (CN); Mingguang Mo, Shanghai (CN); Jintong Yang, Shanghai (CN); Lu Zhou, Shanghai (CN); Yong Chu, Shanghai (CN); Jinyu Fei, Shanghai (CN); Xiangyu Qi, Shanghai (CN)

(73) Assignee: FUDAN UNIVERSITY, Shanghai (CN)

( * ) Notice: Subject to any disclaimer, the term of this patent is extended or adjusted under 35 U.S.C. 154(b) by 0 days.

(21) Appl. No.: 16/967,118

(22) PCT Filed: Jan. 21, 2019

(86) PCT No.: PCT/CN2019/072468
§ 371 (c)(1),
(2) Date: Aug. 3, 2020

(87) PCT Pub. No.: WO2019/154047
PCT Pub. Date: Aug. 15, 2019

(65) Prior Publication Data
US 2021/0032230 A1    Feb. 4, 2021

(30) Foreign Application Priority Data
Feb. 7, 2018 (CN) .......................... 201810124854.9

(51) Int. Cl.
| C07D 413/12 | (2006.01) |
| C07D 261/20 | (2006.01) |
| C07D 401/12 | (2006.01) |
| C07D 413/14 | (2006.01) |
| C07D 417/12 | (2006.01) |

(52) U.S. Cl.
CPC ......... *C07D 413/12* (2013.01); *C07D 261/20* (2013.01); *C07D 401/12* (2013.01); *C07D 413/14* (2013.01); *C07D 417/12* (2013.01)

(58) Field of Classification Search
CPC .. C07D 413/14; C07D 413/12; C07D 417/12; C07D 401/12; C07D 261/20
USPC ...................................... 514/233.8
See application file for complete search history.

(56) References Cited

U.S. PATENT DOCUMENTS 5,668,154 A * 9/1997 Fink ..................... C07D 231/56
514/338

FOREIGN PATENT DOCUMENTS

| WO | 2016029767 A1 | 3/2016 |
| WO | 2019154047 A1 | 8/2020 |

OTHER PUBLICATIONS

Xiang-Yu Qi et al., "Discovery of the selective sphingomyelin synthase 2 inhibitors with the novel structure of oxazolopyridine", Bioogranic & Medicinal Chemistry Letters, May 25, 2017, 5 pages.
Mingguang Mo et al., "Discovery of 4-Benzyloxybenzol[d]isoxazole-3-amine Derivatives as Highly Selective and Orally Efficacious Human Sphingomyelin Synthase 2 Inhibitors that Reduce Chronic Inflammation in db/db Mice", Journal of Medicinal Chemistry, Oct. 8, 2018, 14 pages.
International Search Report issued in International Patent Application PCT/CN2019/072468, dated Apr. 19, 2019 (6 pages).

* cited by examiner

*Primary Examiner* — Kahsay Habte
(74) *Attorney, Agent, or Firm* — Ware, Fressola, Maguire & Barber LLP

(57) ABSTRACT

Alkoxybenzeno five- or six-member heterocyclic amines compounds, their pharmaceutically acceptable salts, and pharmaceutical compositions are used as the active ingredients, and their application in drugs which can prevent and cure diseases caused by abnormal increasing of SM. These diseases caused by abnormal increasing of SM include atherosclerosis, type II diabetes, fatty liver, obesity, metabolic syndromes, enteritis and other inflammatory diseases.

10 Claims, No Drawings

ALKOXYBENZO-FIVE-MEMBERED (SIX-MEMBERED) HETEROCYCLIC AMINE COMPOUND AND PHARMACEUTICAL USE THEREOF

TECHNICAL FIELD

The invention belongs to medicinal chemistry field, which is related to the alkoxybenzeno five- or six-member heterocyclic amines compounds and their pharmaceutical uses, specifically including the alkoxybenzeno five- or six-member heterocyclic amines compounds and their uses in preparing sphingomyelin synthase inhibitors, and uses in prevention or treatment of atherosclerosis, type II diabetes, fatty liver, obesity, enteritis and other inflammatory diseases.

BACKGROUND TECHNOLOGY

According to reports, with the development of economic society and the aging of the population, morbidity and mortality of cardiovascular diseases have increased significantly in recent years, ranking the second place in total mortality, just behind cancer and becoming one of the main diseases threatening human health. Studies showed that atherosclerosis (AS) is one of the main pathological basis of many cardiovascular diseases, thus, making the study of anti-atherosclerosis drugs a hot field of drug development. The studies also conveyed that atherosclerosis is manifested as the yellow substances such as cholesterol and lipid in the endarterium, leading to thrombogenesis and blood supply insufficiency. Although its molecular pathology is not entirely understood, it is widely accepted that among many factors, dyslipidemia is the most important factor in causing atherogenesis and that the formation of atheromas and arteriosclerosis are closely related to the abnormal expression of the lipid component.

Generally speaking, dyslipidemia refers to higher lipid level in plasma and higher blood viscosity caused by lipid metabolism and transfer anomaly, and blood viscosity increasing which mainly characterized by an increase of low-density lipoprotein (LDL) and very low-density lipoprotein (VLDL) and a decrease of high-density lipoprotein (HDL). Therefore, reducing LDL and (or) increasing HDL can play a role in regulating blood lipids and hence plasma lipids regulator can function as the main clinically used drug for anti-atherosclerosis.

The plasma lipid regulators commonly used in clinic mainly includes statins, fibrates, bile acid binding resins, nicotinic acid and so on. Among the above regulators, the statins take effect through inhibiting 3-hydroxy-3-methylglutaryl coenzyme A reductase (HMG CoA reductase), the key enzyme of cholesterol biosynthetic process, to reduce plasma LDL level and the morbidity of coronary heart diseases (Linsel-Nitschke P, Tall A R. *Nat. Rev. Drug. Discov,* 2005, 4, 193-206). However, some studies also show that after treating coronary diseases patients with pravastatin and atorvastatin, though LDL cholesterol level can be reduced in varying degrees, there are still a high incidence rate of cardiovascular diseases among these patients (Cannon C P, Braunwald E, et al. *N Engl J Med,* 2004, 350: 1495-1504). Thus, the treatment effectiveness of simply LDL cholesterol reducing is limited. Furthermore, some studies have shown that statins have other serious side effects such as rhabdomyolysis.

With research progressing, many potential anti-atherosclerosis drug targets proposed in some studies, including sphingomyelin synthase inhibitors, PPAR agonists, apolipoprotein infusion, liver X receptor agonists and phospholipid transfer protein (PLTP) inhibitors. Among them, sphingomyelin (SM) and related metabolic enzymes can change lipoprotein levels while conducting a series of cell-mediated process, which suggested that they play important roles in the development of the atherogenesis.

Studies have shown that SM can induce AS in various pathways, including (1) inhibiting triglyceride (TG) lipolysis (Park T S, Panek R L, et al. *Atherosclerosis.* 2006, 189(2):264-72.); (2) delaying the clearance of atherogenic remnant lipoprotein (Schlitt A, Hojjati M R, et al. *J Lipid Res.* 2005, 46(2):196-200); (3) affecting HDL-mediated cholesterol reverse transport and causing removal cholesterol clearence obstacles (Sano O, Kobayashi A, et al. *J Lipid Res.* 2007, 48(11):2377-84; Marmillot P, Patel S, et al. *Metabolism.* 2007, 56(2):251-9); (4) ceramide and products of SM synthesis and degradation are cell regulators which can affect cell proliferation, activation and apoptosis and hence affect the atherosclerotic plaque growth and stability (Park, T.-S.; Panek, R. L.; et al. *Circulation.* 2004, 110, 3465-3471); (5) LDL enriched in SM has strong cohesion and adhesion power which can make macrophages easy to aggregate on arterial wall to form foam cells thus promote atherogenesis (Fan Y, Shi S, et al. *Arterioscler Thromb Vasc Biol,* 2010, 30:2114-20).

Epidemiological surveys also show that there is an independent correlation between human SM level and AS, and that the plasma concentration of SM is an independent risk factor to AS and make an indicative infuluence in evaluating AS development (Jiang, X.-C.; Paultre, F.; et al. *Arterioscler. Thromb. Vasc.* Biol. 2000, 20, 2614-2618; Zhiqiang Li; Maria J. Baserr; et al. *Biochimica et Biophysica Acta.* 2005, 1735, 130-134); Animal tests shown that inhibiting the de novo biosynthesis of SM can efficiently reduce plasma cholesterol and triglyceride levels and increase the HDL-cholesterol level, thereby can prevent further lesion of AS (Park, T.-S.; Panek, R. L.; et al. *Circulation.* 2004, 110, 3465-3471); Thus, decrease of plasma SM level or inhibition of SM synthesis are rendered to retard or even block athegogenesis.

Studies also show that sphingomyelin synthase (SMS) is the key enzyme of the last step of SM de novo biosynthesis, which can catalyze ceramide and phosphatidylcholine (PC) to synthesis SM. The sphingomyelin synthase (SMS) family has three members: sphingomyelin synthase 1 (SMS1), sphingomyelin synthase 2 (SMS2) and sphingomyelin synthase-related protein (SMSr). In vivo, SMS1 and SMS2 mainly regulate SM synthesis related functions. Among them, SMS1 is mainly distributed in Golgi and is responsible for 60%-80% of SM synthesis, while SMS2 is mainly distributed on the cell membrane and is responsible for 20%-40% of SM synthesis (Tafesse F G, et al. *J Biol Chem.* 2007; 282(24):1753-1747). However, SMSr has no SM synthesis enzyme catalytic function. Yano and other researchers have uncovered that SMS1 knockout of mice caused dysfunction of mitochondria, which increased active oxides and impaired insulin secretion (M. Yano, K., et al. *J Biol Chem.* 2011; 286(5): 3992-4002), The oxidative stress also severely damaged white adipose tissue (WAT) (M. Yano, et al. *PLoS One.* 2013; 8(4): e61380); The knock-out of SMS1 will also affect reproduction (Wittmann A, et al. *PLoS One.* 2016; 11(10):e0164298). But completely knocking out SMS1 will cause adverse reactions such as hearing loss (Lu M H, et al. *J Physiol.* 2012; 590:4029-4044). Therefore, SMS1 may not be an ideal drug target. However, the SMS2 knockout is different from the SMS1 knockout. Not only no serious physiological damage were found in SMS2 knockout animals, but prevention of atherosclerosis and improvement of insulin resistance were found in these animals, etc. (Li Z, Zhang H, et al. *Mol. Cell. Biol.* 2011, 31(20): 4205-4218).

Further studies shown that SMS can regulate SM level directly, and that SMS overexpression is a common phenomenon in atherosclerotic pathological-changed tissue and a key indicators of atherosclerosis (Xian-cheng Jiang; Furcy Paultre; et al. *Arterioscler. Thromb. Vasc Biol.* 2000, 20, 2614-2618; Zhiqiang Li; Tiruneh K. et al. *Biochimica et Biophysica Acta,* 2007, 1771, 1186-1194). In animal tests, it is found that atherosclerotic plaques in arcus aortae are dramatically reduced, and SM and other lipids in brachiocephalic artery are obviously decreased, and have no obvious influence on normal physiology functions in SMS2 and apoE double-gene knockout mice, (Fan Y, Shi S, et al. *Arterioscler. Thromb. Vasc Biol,* 2010, 30:2114-20), which means that the inhibition of SMS catalytic synthesis of SM, the last step of SM biosynthesis cycle, may cause relatively slighter potential adverse effects. In summary, it is believed that SM level reduction induced by SMS2 inhibition is a new methodology for treating atherosclerosis. SMS2 has potential advantages as an anti-atherosclerosis target. Thus the selective SMS2 inhibitors might become a novel drug candidate for AS.

Furthermore, some studies have shown that SMS2 deficiency can prevent obesity and insulin resistance caused by high-fat diet; meanwhile, it is difficult to observe significant mature fatty plaques in the livers of SMS2 knock-out mice, suggesting that SMS2 can take part in formation of liver fatty plaques and can induce obesity and type II diabetes (Susumu Mitsutake, Kota Zama, et al. *Journal of Biological Chemistry.* 2011, 286(32), 28544-28555). Plasma SM decrease caused by SMS2 deficiency can improve animal tissue and physical insulin sensibility (Li Z, Zhang H, et al. *Mol. Cell. Biol.* 2011, 31(20): 4205-4218). SMS2 gene knockout can make insulin-targeted tissues such as bones and muscles in mice improve glucose absorption, thereby lowering blood glucose levels (Sugimoto, Masayuki, et al. *Biochimica et Biophysica Acta* 1861 2016, 688-702). Sphingomyelin (d18:1/16) was found to accumulate in the glomeruli of diabetic patients, and was also confirmed in mice on a high-fat diet compared to the control; in vitro, adding SM (d18:1/16) to cells can increase ATP levels and reduce AMPK level. Studies have shown that activity inhibition of sphingomyelin synthase can reverse the above phenomenon, which means that SM (d18:1/16) as a regulatory factor can regulate the ratio of ATP to AMP in diabetic nephropathy and obesity; and it has been determined that inhibition of sphingomyelin synthase can reduce the high ratio of ATP to AMP in diabetic nephropathy and obesity (S. Miyamoto et al. *E Bio Medicine* 2016, (7) 121-134). Therefore, SMS small-molecule inhibitors can prevent and treat type II diabetes, obesity, fatty liver, and other metabolic syndromes.

It is reported that SMS2 gene knockout can significantly reduce inflammation, insulin resistance and other metabolic syndromes in mice fed with a high-fat diet (Susumu Mitsutake, Kota Zama, et al. *Journal of Biological Chemistry.* 2011, 286(32), 28544-28555). In the study of the effect of sphingomyelin type on inflammation, it was found that adding a very long chain of sphingomyelin (d18:1/24:0) in vitro can directly activate macrophages; and that the long-chain sphingomyelin (d18:1/24:0) in SMS2 knockout mice was significantly reduced compared with the SMS2 gene knockout and wild type mice. Thus, from the molecular mechanism phenotype, it can also be concluded that inhibition of SMS2 activity has anti-inflammatory effects (Hideaki Sakamoto. et al. *Biochemical and Biophysical Research Communications,* 2016, 1-6). The latest study reports that the deletion of SMS2 gene can significantly improve murine colitis induced by dextran sodium sulfate (DSS), and can also reduce the incidence of intestinal cancer induced by DSS (Ohnishi, T et al, *FASEB J,* 2017, 31(9), 3816-3830). Therefore, SMS2 small molecule inhibitors may be used to prevent and treat inflammation-related diseases such as enteritis and intestinal cancer, etc.

At present, it was reported that D609 is one of the SMS inhibitors (Aimin Meng; Chiara Luberto; et al. *Experimental Cell Research,* 2004, 292, 385-392) with a weak inhibitory activity ($IC_{50}$=375 μM) and a highly unstable xanthate structure (Bai, A. et al. *J. Pharmacol. Exp. Ther.* 2004, 309, 1051-1059) and a short half-life time. By the virtual screening of the three-dimensional structure model of sphingomyelin synthase based on homology modeling, a small molecule sphingomyelin synthase inhibitor compound D2 was discovered (Xiaodong Deng, Fu Lin, et al. *European Journal of Medicinal Chemistry,* 2014, 73, 1-7). Although its inhibitory activity on SMS2 in vitro was enhanced compared with D609, compound D2 still has the following defects: its inhibitory activity needs to be improved, and it contains cyano groups with a greater potential risk of toxicity and poor physical and chemical properties such as water solubility and stability. The uncovered 2-alkoxy benzene fomyl arylamine compounds are a class of highly active sphingomyelinase inhibitors, but their activity is in the micromolar range, and there is no report about the selectivity of SMS1 and SMS2 (WO2016029767A1). Takeda Corporation of Japan uncovered a class of 2-quinolinone derivatives with a highly selective SMS2 inhibitory effect. The 293 cell line was used to highly express human-derived SMS2, and then the supernatant of the cell homogenate was used as the enzyme source, the inhibitory activity was measured and the $IC_{50}$ value of 2-quinolinone derivatives was 6.5 nM (R. Adachi et al. *European Journal of Medicinal Chemistry,* 2017, 136, 283-293); Its activity and selectivity are high, but due to its relatively large molecular weight and high c Log P (MW 625.57; c Log P 6.47), there is certain druggability problems in it. It has been reported that 2-benzyloxyphenyloxazolopyridines have micromolar SMS2 inhibition activity and good selectivity, and the inhibitor activity against pure SMS1 and SMS2 enzyme is reported for the first time (Qi et al. *Bioorg Med Chem Lett,* 2017, 27(15), 3511-3515), but its activity needs to be further improve. Hokkaido University of Japan has published an SMS2 inhibitor with an $IC_{50}$ value of 130 nM on human protein-expressing cells. However, its human-derived SMS1 inhibition activity has not been reported (JP2017128518A).

SUMMARY OF THE INVENTION

This invention aims to conquer the drawbacks and defects of existing technology and shows alkoxybenzeno five- or six-member heterocyclic amines and their pharmaceutical use, involving alkoxybenzeno five- or six-member heterocyclic amines and their uses in preparing SMS inhibitors and in prevention and treatment of atherosclerosis, type II diabetes, fatty liver, obesity, and metabolic syndromes, as well as enteritis and other inflammatory diseases.

The first aim of the present invention is to provide alkoxybenzeno five- or six-member heterocyclic amines compounds and their pharmaceutically acceptable salts. The above alkoxybenzeno five- or six-member heterocyclic amines includes free base and salts of those compounds shown in scheme I.

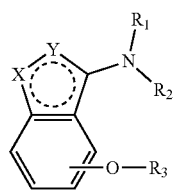

(I)

In the scheme,

X is chosen from one or two of oxygen atom, nitrogen atom, sulfur atom and carbon atom.

Y is chosen from one or two of oxygen atom, nitrogen atom, sulfur atom and carbon atom.

The compounds obtained by the combination of X and Y are the following structures but not limited to these:

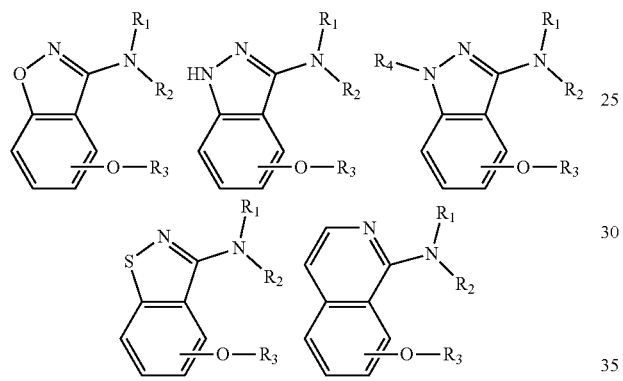

$R_4$ is chosen from methyl, hydrogen atom or ethyl;

$R_1$ is chosen from benzene ring, heterocycle or acyl group.

The heterocyclic compounds are the following structures but not limited to these:

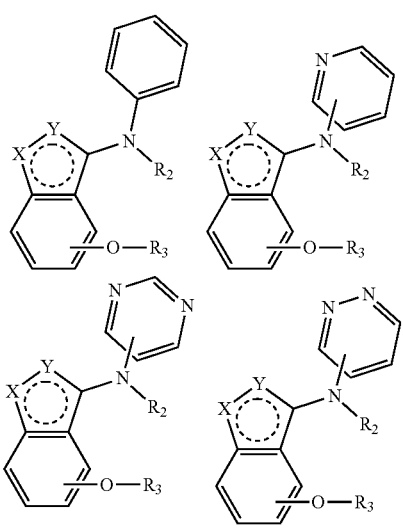

The acyl compounds are the following structures but not limited to these:

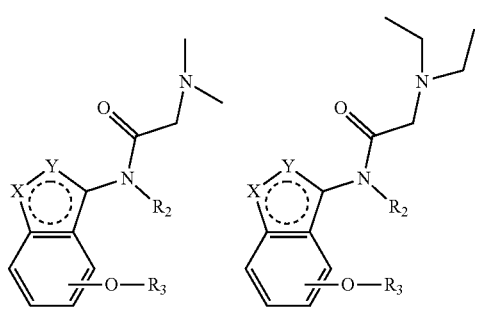

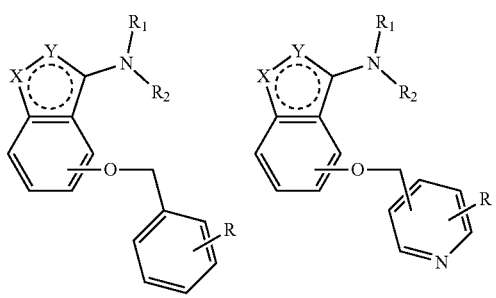

$R_2$ is chosen from any one of hydrogen atom, methyl, ethyl, and propyl.

$R_3$ is chosen from alkoxy, phenylmethylene and heterocyclic methylene, including but not limited to benzyloxy, pyridine methylene, alkane with 1-8 carbons, or aminoalkyl with 1-8 carbons.

The $R_3$ compounds are the following structures but not limited to these:

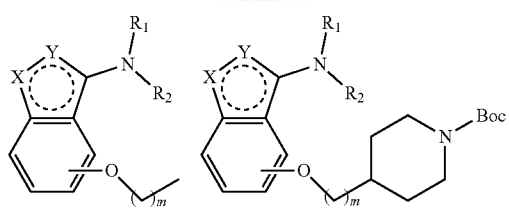
R is chosen from but not limited to o-F, m-F, p-F, o-Cl, m-Cl, p-Cl, o-Me, m-Me, p-Me, o-CF3, m-CF3, p-CF3, o-OCF3, m-OCF3, p-OCF3, o-OMe, m-OMe, p-OMe, o-CN, m-CN, p-CN, o-Et, and one or two substituents in aromatic ring. The range of m is from 0 to 5.
It can be further described as compounds of Scheme I-1 to I-40.
Scheme I-1
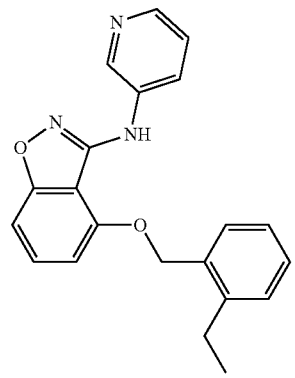
Scheme I-2
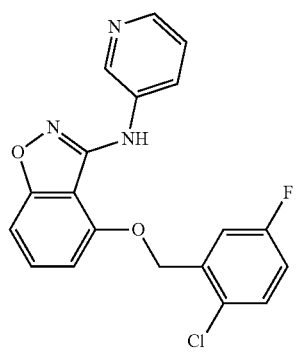
Scheme I-3
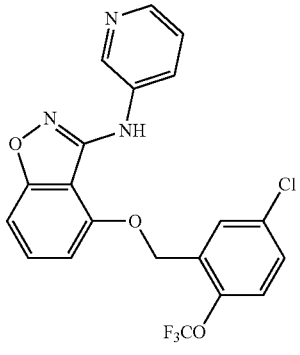
Scheme I-4
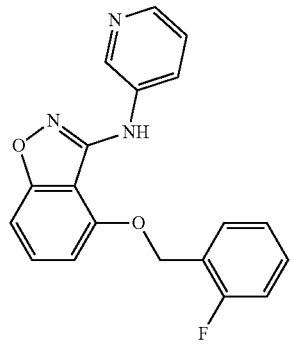
Scheme I-5
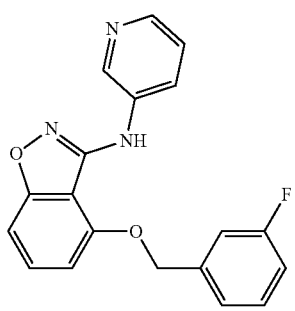
Scheme I-6
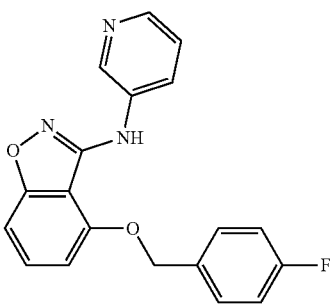
Scheme I-7
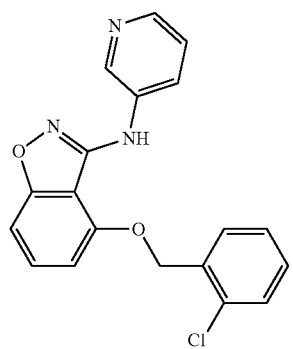
Scheme I-8
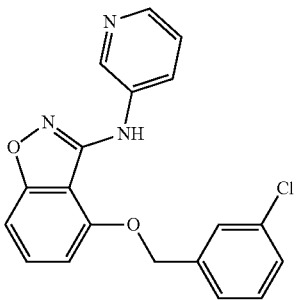

Scheme I-9
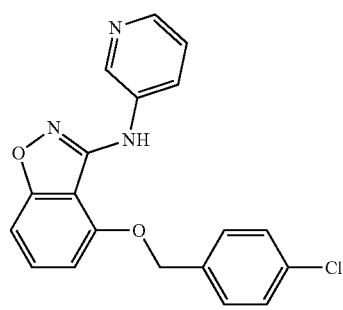
Scheme I-10
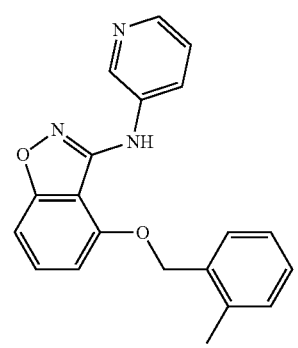
Scheme I-11
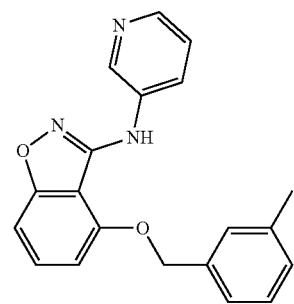
Scheme I-12
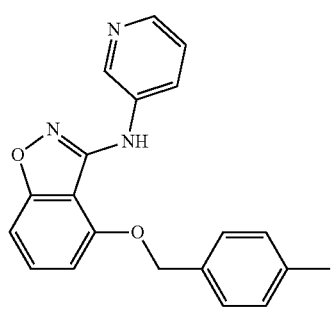
Scheme I-13
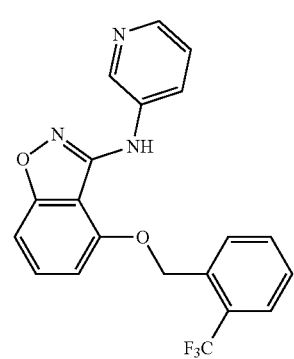
Scheme I-14
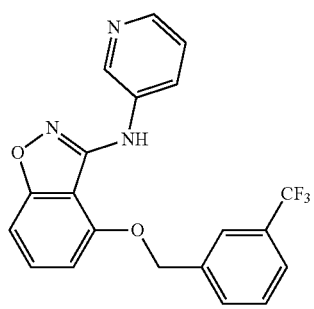
Scheme I-15
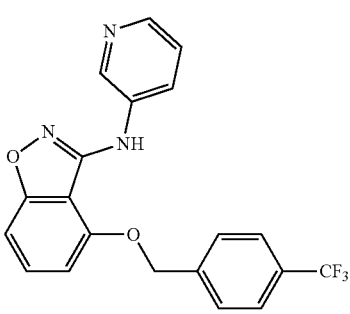
Scheme I-16
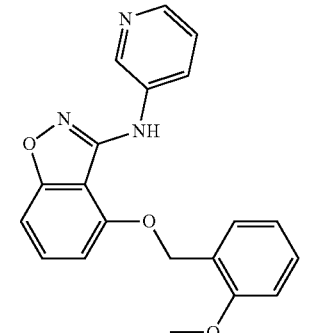
Scheme I-17
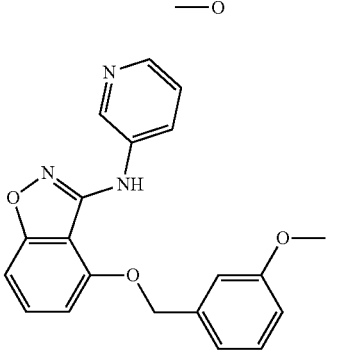
Scheme I-18
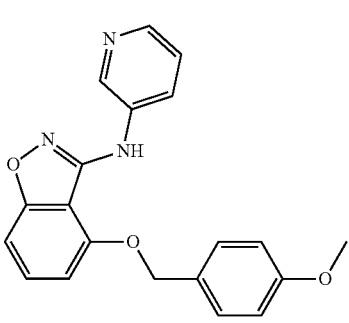

Scheme I-19
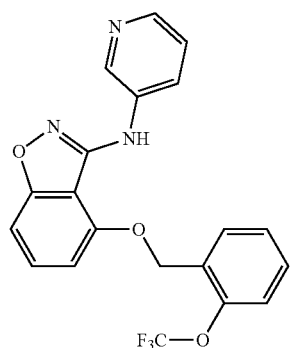
Scheme I-20
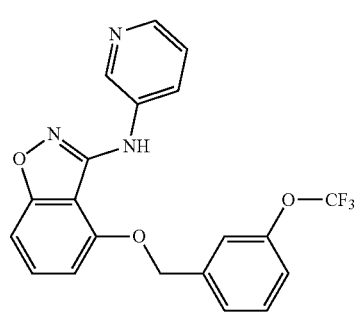
Scheme I-21
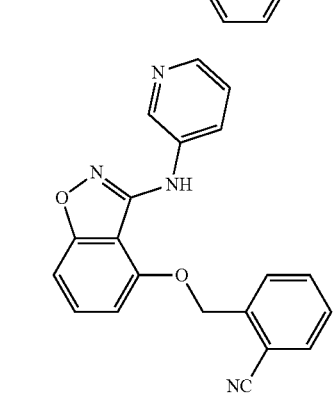
Scheme I-22
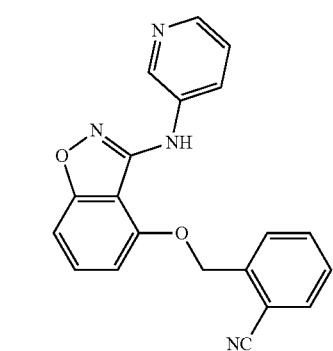
Scheme I-23
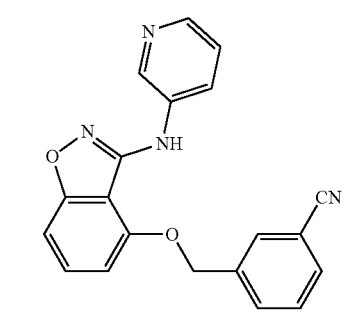
Scheme I-24
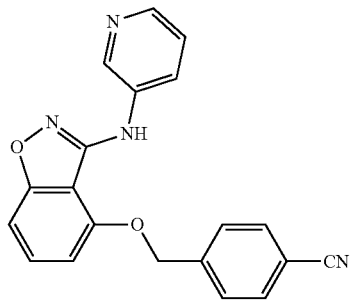
Scheme I-25
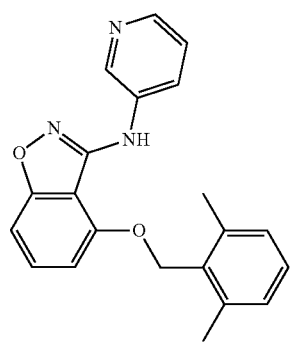
Scheme I-26
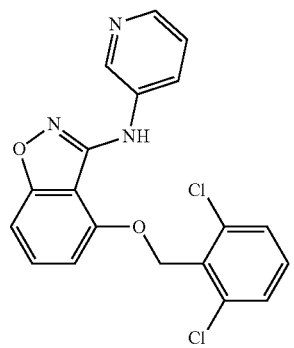
Scheme I-27
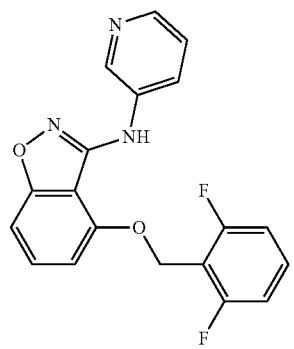

Scheme I-28
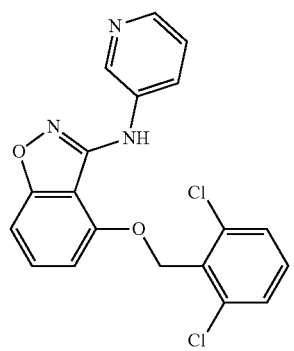
Scheme I-29
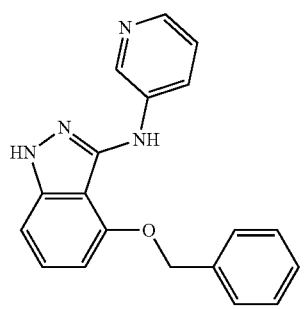
Scheme I-30
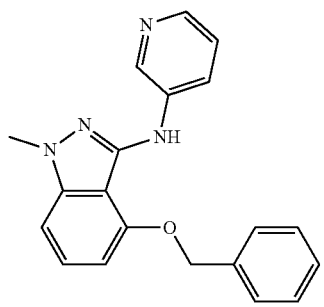
Scheme I-31
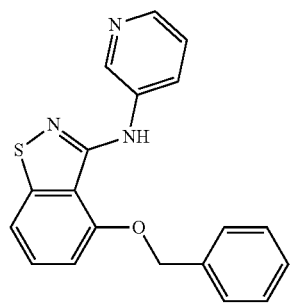
Scheme I-32
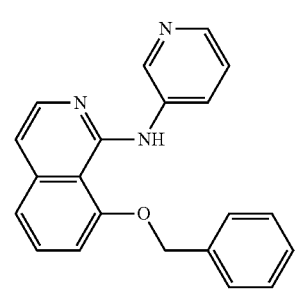
Scheme I-33
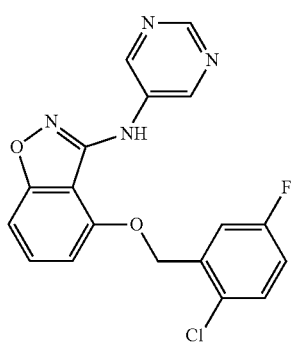
Scheme I-34
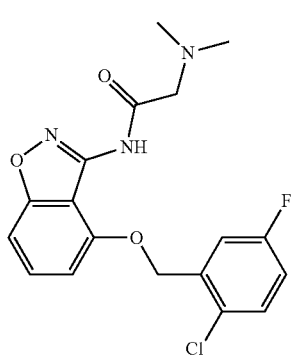
Scheme I-35
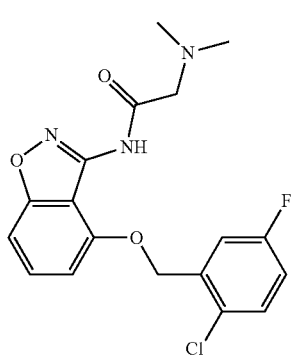
Scheme I-36
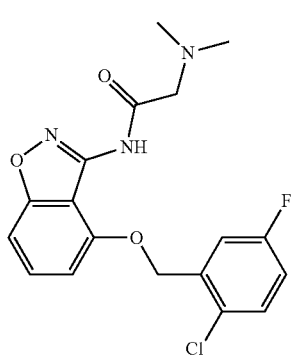

Scheme I-37

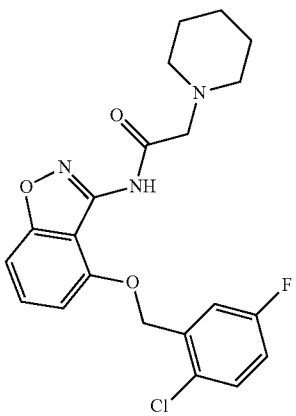

Scheme I-38

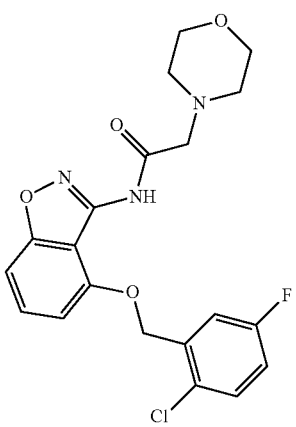

Scheme I-39

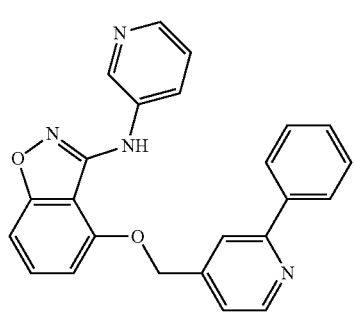

Scheme I-40

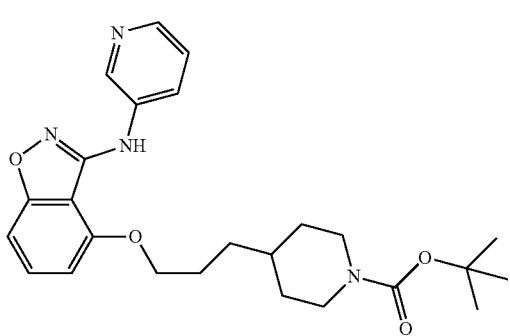

The compounds of the present invention contain alkaline groups which can form salts with acids and can be transformed into derivatives salt through nomal ways. The above salts includes organic acid salts such as acetate, citrate, fumarate, maleate, oxalate, malate, citrate, succinate, tartrate, lactate, camphor sulfonate, benzene sulfonate, p-toluenesulfonate, methanesulfonate, trifluoroacetate, triflate, and the like; inorganic acid salts such as hydrohalic acids (hydrofluoric acid, hydrochloric acid, hydrobromic acid, hydroiodic acid), sulfate, phosphate, nitrate and the like, or with amino acids, such as glutamic acid and aspartic acid to form glutamate and aspartate. The preferred salts are the hydrochloride and the hydrobromide.

Solvates of alkoxybenzeno five- or six-member heterocyclic amines compounds are also protected by the present invention. The preferred solvates are water, ethanol, and methanol.

The second aim of the present invention is to show the use of alkoxybenzeno five- or six-member heterocyclic amines in preparing SMS2 small-molecule inhibitors. This invention evaluate SMS inhibitory activity of alkoxybenzeno five- or six-member heterocyclic amines shown as scheme I through reported HPLC fluorogenic quantitative detecting method (Xiaodong Deng; Hong Sun; et al. *Analytical Letters*, 2012, 45:12, 1581-1589), which can make it possible to calculate the catalytic activity difference of SMS treated with inhibitors or not through content changes of NBD-ceramide and NBD-sphingomyelin.

Activity tests with HPLC fluorogenic quantitative detecting method show that alkoxybenzeno five- or six-member heterocyclic amines shown as scheme I has a sub-micromolar sphingomyelin synthase inhibitory activity and have superior SMS subtype selectivity and selectively inhibit SMS2. The effective concentration of these compounds for SMS1 and SMS2 is several hundred times different. These compounds are effective compounds inhibiting SMS2; High-performance liquid chromatography (HPLC) fluorescence quantitative method was used to detect the inhibitory activity of the compounds on sphingomyelin synthase 2 (SMS2).

The further aim of this invention is to provide the use of alkoxybenzeno five- or six-member heterocyclic amines as scheme I and their salts or solvate in preventing and treating atherosclerosis, fatty liver, obesity, type II diabetes, metabolic syndromes, enteritis and other inflammatory diseases.

The present invention experimentally confirmed that the disclosed compounds in the present invention have significant inhibitory activities against SMS2 and ideal physicochemical properties such as stability and water solubility. Furthermore, there is no potential toxic group in these compounds, which suggests few potential reverse effects. These compounds can be used to prevent and treat atherosclerosis, type II diabetes, fatty liver, obesity, and inflammation caused by SM abnormal increase.

The drugs mentioned above may also contain one or more pharmaceutically acceptable carriers, including conventional diluents, excipients, fillers, binders, humectants, disintegrants, absorption enhancers, surfactants, adsorption carrier, lubricants and the like, and flavoring agents, sweetening and the like if necessary.

The beneficial effect of the present invention is that the alkoxybenzeno five- or six-member heterocyclic amines compounds are a class of novel SMS inhibitors which have sub-micromolar sphingomyelin synthase inhibitory activities, inhibitoy selectivities for SMS2 subtype and have a real potentiality and prospects to be developed as drugs to cure atherosclerosis, type II diabetes, fatty liver, obesity, and metabolic syndromes, as well as enteritis and other inflammatory diseases.

DETAILED DESCRIPTION

Application Case 1: Preparation of 4-((2-ethylbenzyl)oxy)-N-(pyridin-3-yl)benzo[d]isoxazol-3-amine (Scheme I-1)

1. Synthesis of 2-(Benzyloxy)-6-fluorobenzonitrile (Compound 4)

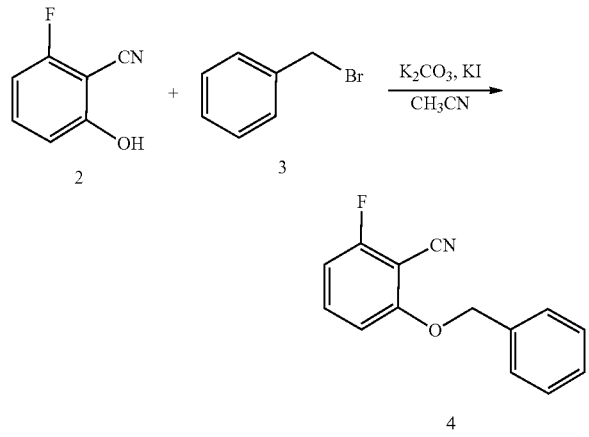

To a mixture of 10.00 g (73.0 mmol, 2.0 eq) $K_2CO_3$, 200 mg KI and 5.00 g 2-fluoro-6-hydroxybenzonitrile (36.5 mmol, 1.0 eq) in 100 ml acetonitrile, then 6.55 g (38.3 mmol, 1.05 eq) benzyl bromide was added to the mixture, and the whole was stirred at room temperature for 12 h. After the reaction was complete, most of the solution was removed under reduced pressure, water was added to the residue and extracted with EA, the organic layers washed with saturated sodium chloride solution, dried over $Na_2SO_4$, filtered, and concentrated. The residue was purified with column chromatography (PE/EA=15:1) to give compound 4, 8.0 g white solid, yield 96%.

The structure is confirmed correct and data are as follow: MS (ESI) (m/z): 228.0 (M+H)+. 1H NMR (400 MHz, DMSO-$d_6$) δ 7.73-7.62 (m, 1H), 7.43 (d, J=7.0 Hz, 2H), 7.38 (t, J=7.4 Hz, 2H), 7.32 (d, J=7.1 Hz, 1H), 7.16 (d, J=8.7 Hz, 1H), 7.03 (t, J=8.8 Hz, 1H), 5.27 (s, 2H).

2. Synthesis of 4-(Benzyloxy)benzo[d]isoxazol-3-amine (Compound 6)

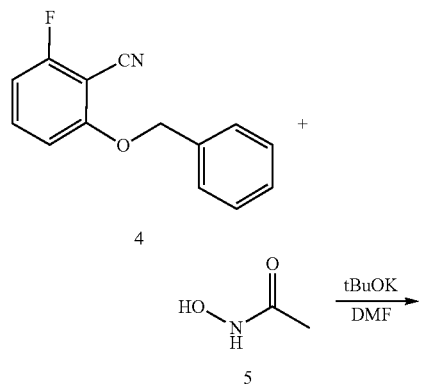

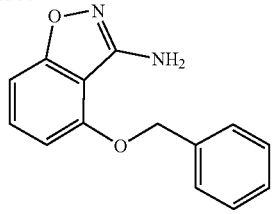

To a solution of 4.0 g acetohydroxamic acid (53.3 mmol, 1.5 eq) in 150 ml dry DMF, then add 6.0 g t-BuOK (53.3 mmol, 1.5 eq) and stir at rt for 0.5 h under nitrogen. Then, 8.0 g 2-(Benzyloxy)-6-fluorobenzonitrile (35.2 mmol, 1.0 eq) was added in batches. After an additional 6 h of stirring at rt, most of the solution was removed under reduced pressure, water was added to the residue and extracted with EA, the organic layers washed with saturated sodium chloride solution, dried over $Na_2SO_4$, filtered, and concentrated. The crude product was purified by recrystallization with a mixed solvent of DCM and PE to give 2.0 g compound 6, yield 24%.

The structure is confirmed correct and data are as follow: MS(ESI) (m/z): 241.0 (M+H)+. 1H NMR (400 MHz, DMSO-$d_6$) δ 7.50 (d, J=6.8 Hz, 2H), 7.42-7.34 (m, 3H), 7.34-7.28 (m, 1H), 6.96 (d, J=8.4 Hz, 1H), 6.76 (d, J=8.0 Hz, 1H), 5.86 (s, 2H), 5.29 (s, 2H).

3. Synthesis of 4-(Benzyloxy)-N-(pyridin-3-yl)benzo[d]isoxazol-3-amine (Compound 8)

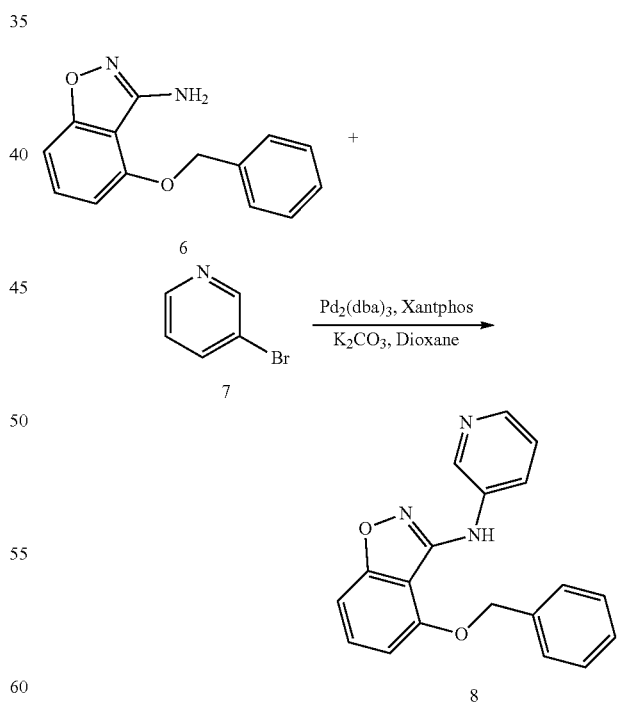

A mixture of 3.0 g 4-(benzyloxy)benzo[d]isoxazol-3-amine (12.5 mmol, 1.0 eq) and 3.0 g 3-bromopyridine (18.75 mmol, 1.5 eq), 1.14 g $Pd_2(dba)_3$(1.25 mmol, 0.1 eq), 1.44 g Xantphos (2.50 mmol, 0.2 eq), and 3.45 g anhydrous potassium carbonate (25.0 mmol, 2.0 eq) in 50 ml dioxane. After nitrogen substitution three times, heat to 125° C. and reflux for 12 h under nitrogen protection. After the reaction was complete, most of the solution was removed under reduced pressure, water was added to the residue and extracted with EA, the organic layers washed with saturated sodium chloride solution, dried over Na$_2$SO$_4$, filtered, and concentrated. The residue was purified with column chromatography (PE/EA=3:2) to give compound 8, 3.1 g beige solid, yield 78%.

The structure is confirmed correct and data are as follow: MS(ESI) (m/z): 318.0 (M+H)$^+$. $^1$H NMR (400 MHz, DMSO-d$_6$) δ 8.73 (d, J=2.8 Hz, 1H), 8.28 (s, 1H), 8.18 (dd, J=4.7, 1.4 Hz, 1H), 8.09-8.01 (m, 1H), 7.54 (d, J=7.5 Hz, 2H), 7.47 (t, J=8.2 Hz, 1H), 7.43-7.34 (m, 3H), 7.31 (t, J=7.2 Hz, 1H), 7.11 (d, J=8.4 Hz, 1H), 6.85 (d, J=8.0 Hz, 1H), 5.41 (s, 2H).

4. Synthesis of 3-(pyridin-3-ylamino)benzo[d]isoxazol-4-ol (Compound 9)

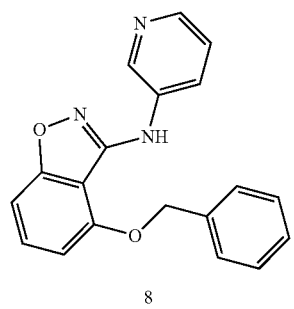

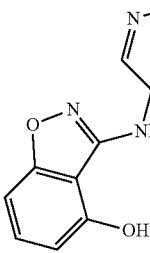

A mixture of 3.1 g 4-(Benzyloxy)-N-(pyridin-3-yl)benzo[d]isoxazol-3-amine (9.8 mmol, 1.0 eq) in 20 ml 40% HBr aqueous solution and 20 ml HOAc was heated to 65° C. and reacted for 12 h. After the reaction was complete, most of the solution was removed under reduced pressure, then neutralize with saturated sodium carbonate aqueous solution to pH=8, add appropriate EA to extract, then obtain a suspension, filter to obtain a part of gray solid product, the mother liquor continues to extract with EA, the organic layers washed with saturated sodium chloride solution, dried over Na$_2$SO$_4$, filtered, and concentrated. The residue was purified with column chromatography (DCM/MeOH=20:1) to give compound 9, 1.4 g gray solid, yield 63%.

The structure is confirmed correct and data are as follow: MS (ESI) (m/z): 228.0 (M+H)$^+$. $^1$H NMR (400 MHz, DMSO-d$_6$) δ 11.20 (s, 1H), 8.90 (d, J=2.7 Hz, 1H), 8.35 (s, 1H), 8.20-8.13 (m, 2H), 7.40-7.32 (m, 2H), 6.97 (d, J=8.3 Hz, 1H), 6.65 (d, J=7.8 Hz, 1H).

5. Synthesis of 2-ethylbenzyl Bromide (Compound 11)

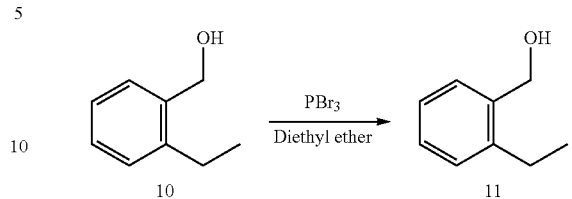

Dissolve 250 mg 2-ethylbenzyl alcohol (1.84 mmol, 1.0 eq) in 10 mL anhydrous ether, cool to 0° C. with an ice water bath, add 191 mg of phosphorus tribromide (0.72 mmol, 0.5 eq). After reacting at 0° C. for 15 min, the ice-water bath was removed, wait for the temperature to rise to room temperature and react for 2 h. Then the mixture was cooled to 0° C. with ice-water bath, water was added to the residue and extracted with EA, the organic layers washed with saturated sodium chloride solution, dried over Na$_2$SO$_4$, filtered, and concentrated to give compound 11, 250 mg oily substance, yield 89%. The crude product was used without purification in the next step directly.

6. Synthesis of 4-((2-ethylbenzyl)oxy)-N-(pyridin-3-yl)benzo[d]isoxazol-3-amine (Scheme I-1)

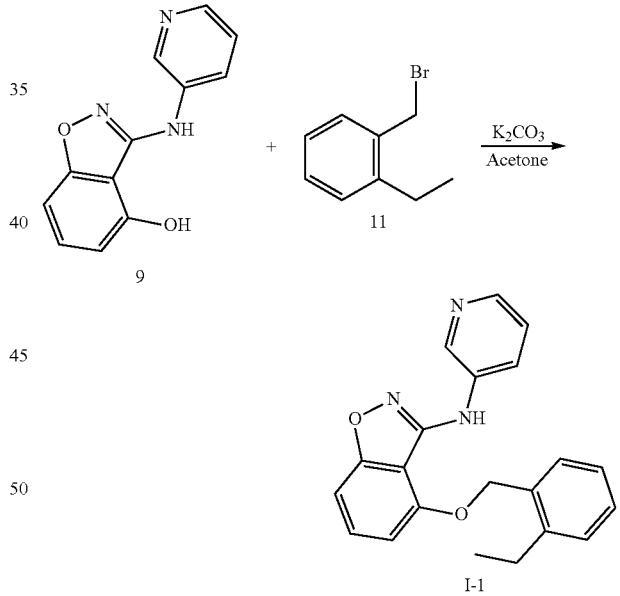

50 mg 3-(pyridin-3-ylamino)-4-hydroxybenzo[d]isoxazole (0.22 mmol, 1.0 eq), 44 mg 2-ethylbenzyl bromide (0.22 mmol, 1.0 eq) and 61 mg anhydrous potassium carbonate (0.44 mmol, 2.0 eq) was mixed, and 5 mL acetone was added, then the mixture was reacted at room temperature for 3 h, water was added, extracted with EA, the organic layers washed with saturated sodium chloride solution, dried over Na$_2$SO$_4$, filtered, and concentrated. The residue was purified with column chromatography (PE/EA=2:1) to give compound I-1, 30 mg white solid, yield 39%.

The structure is confirmed correct and data are as follow: MS (ESI) (m/z): 346.0 (M+H)$^+$. $^1$H NMR (400 MHz, DMSO-d$_6$) δ 8.64 (d, J=2.7 Hz, 1H), 8.22 (s, 1H), 8.15 (d, J=4.6 Hz, 1H), 8.00 (dt, J=8.6, 2.0 Hz, 1H), 7.48 (t, J=7.8 Hz, 2H), 7.35 (dd, J=8.4, 4.7 Hz, 1H), 7.28-7.21 (m, 2H), 7.22-7.15 (m, 1H), 7.11 (d, J=8.4 Hz, 1H), 6.89 (d, J=8.0 Hz, 1H), 5.44 (s, 2H), 2.73 (t, J=7.5 Hz, 2H), 1.11 (t, J=7.5 Hz, 3H).

Application Case 2: Synthesis of Scheme I-2, I-4~I-27

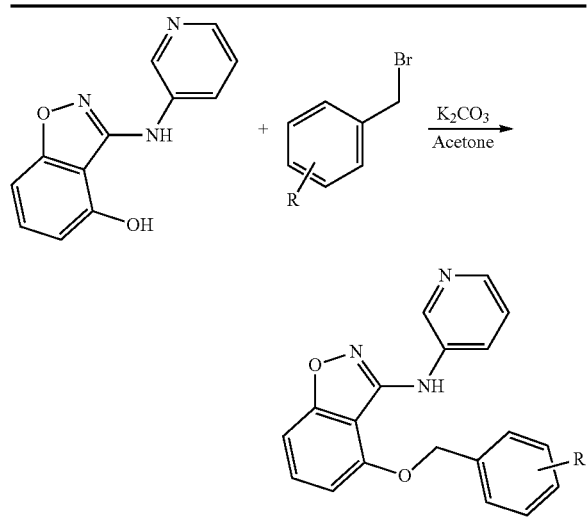

| Scheme I | R | Yield (%) |
|---|---|---|
| I-2 | 2-Cl,5F | 59 |
| I-4 | 2-F | 52 |
| I-5 | 3-F | 58 |
| I-6 | 4-F | 70 |
| I-7 | 2-Cl | 55 |
| I-8 | 3-Cl | 60 |
| I-9 | 4-Cl | 65 |
| I-10 | 2-Me | 50 |
| I-11 | 3-Me | 56 |
| I-12 | 4-Me | 65 |
| I-13 | 2-CF$_3$ | 40 |
| I-14 | 3-CF$_3$ | 60 |
| I-15 | 4-CF$_3$ | 65 |
| I-16 | 2-OMe | 38 |
| I-17 | 3-OMe | 49 |
| I-18 | 4-OMe | 50 |
| I-19 | 2-OCF$_3$ | 43 |
| I-20 | 3-OCF$_3$ | 60 |
| I-21 | 4-OCF$_3$ | 66 |
| I-22 | 2-CN | 45 |
| I-23 | 3-CN | 50 |
| I-24 | 4-CN | 70 |
| I-25 | 2-Me,6-Me | 35 |
| I-26 | 2-Cl,6-Cl | 38 |
| I-27 | 2-F,6-F | 40 |

Referring to reaction conditions of the fifth step of synthesizing Scheme I-1 in Application case 1, reaction of 3-(Pyridin-3-ylamino)benzo[d]isoxazol-4-ol with the corresponding substituted benzyl bromide gives the corresponding target compounds Scheme I-2 and I-4 to I-27, that is:
4-((2-Chloro-5-fluorobenzyl)oxy)-N-(pyridin-3-yl)benzo[d]-isoxazol-3-amine (Scheme I-2); 4-((2-fluorobenzyl)oxy)-N-(pyridin-3-yl)benzo[d]isoxazol-3-amine (Scheme I-4); 4-((3-fluorobenzyl)oxy)-N-(pyridin-3-yl)benzo[d]isoxazol-3-amine (Scheme I-5); 4-((4-fluorobenzyl)oxy)-N-(pyridin-3-yl)benzo[d]isoxazol-3-amine (Scheme I-6); 4-((2-chlorobenzyl)oxy)-N-(pyridin-3-yl)benzo[d]isoxazol-3-amine (Scheme I-7); 4-((3-chlorobenzyl)oxy)-N-(pyridin-3-yl)benzo[d]isoxazol-3-amine (Scheme I-8); 4-((4-chlorobenzyl)oxy)-N-(pyridin-3-yl)benzo[d]isoxazol-3-amine (Scheme I-9); 4-((2-methylbenzyl)oxy)-N-(pyridin-3-yl)benzo[d]isoxazol-3-amine (Scheme I-10); 4-((3-methylbenzyl)oxy)-N-(pyridin-3-yl)benzo[d]isoxazol-3-amine (Scheme I-11); 4-((4-methylbenzyl)oxy)-N-(pyridin-3-yl)benzo[d]isoxazol-3-amine (Scheme I-12);
4-((2-Trifluoromethylbenzyl)oxy)-N-(pyridin-3-yl)benzo[d]isoxazole-3-amine (Scheme I-13);
4-((3-Trifluoromethylbenzyl)oxy)-N-(pyridin-3-yl)benzo[d]isoxazole-3-amine (Scheme I-14);
4-((4-Trifluoromethylbenzyl)oxy)-N-(pyridin-3-yl)benzo[d]isoxazole-3-amine (Scheme I-15);
4-((2-Methoxybenzyl)oxy)-N-(pyridin-3-yl)benzo[d]isoxazol-3-amine (Scheme I-16);
4-((3-Methoxybenzyl)oxy)-N-(pyridin-3-yl)benzo[d]isoxazol-3-amine (Scheme I-17);
4-((4-Methoxybenzyl)oxy)-N-(pyridin-3-yl)benzo[d]isoxazol-3-amine (Scheme I-18);
4-((2-Trifluoromethoxybenzyl)oxy)-N-(pyridin-3-yl)benzo[d]-isoxazol-3-amine (Scheme I-19);
4-((3-Trifluoromethoxybenzyl)oxy)-N-(pyridin-3-yl)benzo[d]-isoxazol-3-amine (Scheme I-20);
4-((4-Trifluoromethoxybenzyl)oxy)-N-(pyridin-3-yl)benzo[d]-isoxazol-3-amine (Scheme I-21);
4-((2-Cyanobenzyl)oxy)-N-(pyridin-3-yl)benzo[d]isoxazol-3-amine (Scheme I-22); 4-((3-Cyanobenzyl)oxy)-N-(pyridin-3-yl)benzo[d]isoxazol-3-amine (Scheme I-23); 4-((4-Cyanobenzyl)oxy)-N-(pyridin-3-yl)benzo[d]isoxazol-3-amine (Scheme I-24);
4-((2,6-Dimethylbenzyl)oxy)-N-(pyridin-3-yl)benzo[d]isoxazol-3-amine (Scheme I-25);
4-((2,6-Dichlorobenzyl)oxy)-N-(pyridin-3-yl)benzo[d]isoxazol-3-amine (Scheme I-26);
4-((2,6-Difluorobenzyl)oxy)-N-(pyridin-3-yl)benzo[d]isoxazol-3-amine (scheme I-27).

The structures were confirmed correct and data are as follow:

Scheme I-2 MS(ESI) (m/z): 370.1 (M+H)$^+$. $^1$H NMR (400 MHz, DMSO-d$_6$) δ 8.72 (d, J=2.7 Hz, 1H), 8.32 (s, 1H), 8.18 (dd, J=4.7, 1.5 Hz, 1H), 8.05 (d, J=8.4 Hz, 1H), 7.64-7.51 (m, 3H), 7.38 (dd, J=8.4, 4.7 Hz, 1H), 7.29 (dt, J=8.7, 4.3 Hz, 1H), 7.20 (d, J=8.4 Hz, 1H), 6.90 (d, J=8.0 Hz, 1H), 5.46 (s, 2H).

Scheme I-4 MS(ESI) (m/z): 336.1 (M+H)$^+$. $^1$H NMR (400 MHz, DMSO-d$_6$) δ 8.67 (d, J=2.7 Hz, 1H), 8.20 (s, 1H), 8.15 (d, J=4.6 Hz, 1H), 8.00 (d, J=8.5 Hz, 1H), 7.60 (t, J=7.6 Hz, 1H), 7.48 (t, J=8.2 Hz, 1H), 7.35 (td, J=9.2, 8.7, 5.6 Hz, 2H), 7.21 (dt, J=15.3, 8.6 Hz, 2H), 7.12 (d, J=8.6 Hz, 1H), 6.89 (d, J=8.1 Hz, 1H), 5.44 (s, 2H).

Scheme I-5 MS(ESI) (m/z): 336.1 (M+H)$^+$. $^1$H NMR (400 MHz, DMSO-d$_6$) δ 8.75 (d, J=2.7 Hz, 1H), 8.34 (s, 1H), 8.16 (dd, J=4.7, 1.5 Hz, 1H), 8.06 (ddd, J=8.4, 3.0, 1.5 Hz, 1H), 7.48 (d, J=8.2 Hz, 1H), 7.46-7.39 (m, 2H), 7.36 (dd, J=8.7, 3.9 Hz, 2H), 7.12 (d, J=8.4 Hz, 1H), 6.82 (d, J=8.0 Hz, 1H), 5.41 (s, 2H).

Scheme I-6 MS(ESI) (m/z): 336.1 (M+H)$^+$. $^1$H NMR (400 MHz, DMSO-d$_6$) δ 8.71 (s, 1H), 8.25 (s, 1H), 8.14 (d, J=4.6 Hz, 1H), 8.02 (d, J=8.4 Hz, 1H), 7.65-7.51 (m, 2H), 7.43 (t, J=8.2 Hz, 1H), 7.33 (dd, J=8.3, 4.7 Hz, 1H), 7.18 (t, J=8.7 Hz, 2H), 7.08 (d, J=8.4 Hz, 1H), 6.81 (d, J=8.1 Hz, 1H), 5.35 (s, 2H).

Scheme I-7 MS(ESI) (m/z): 336.1 (M+H)$^+$. $^1$H NMR (400 MHz, DMSO-d$_6$) δ 8.67 (s, 1H), 8.23 (s, 1H), 8.15 (s, 1H), 8.01 (d, J=8.4 Hz, 1H), 7.60 (s, 1H), 7.49 (q, J=8.9, 7.5 Hz, 2H), 7.34 (s, 3H), 7.14 (d, J=8.4 Hz, 1H), 6.85 (d, J=7.9 Hz, 1H), 5.46 (s, 2H).

Scheme I-8 MS(ESI) (m/z): 352.1 (M+H)+. $^1$H NMR (400 MHz, DMSO-$d_6$) δ 8.77 (d, J=2.6 Hz, 1H), 8.33 (s, 1H), 8.21-8.14 (m, 1H), 8.11-8.03 (m, 1H), 7.67 (s, 1H), 7.48 (dd, J=9.4, 7.2 Hz, 2H), 7.37 (td, J=10.2, 8.7, 5.8 Hz, 3H), 7.13 (d, J=8.4 Hz, 1H), 6.83 (d, J=8.0 Hz, 1H), 5.41 (s, 2H).

Scheme I-9 MS(ESI) (m/z): 352.1 (M+H)+. $^1$H NMR (400 MHz, DMSO-$d_6$) δ 8.77 (d, J=2.7 Hz, 1H), 8.30 (s, 1H), 8.19 (d, J=4.6 Hz, 1H), 8.11-8.02 (m, 1H), 7.58 (d, J=8.1 Hz, 2H), 7.45 (dd, J=8.1, 6.2 Hz, 3H), 7.37 (dd, J=8.4, 4.7 Hz, 1H), 7.12 (d, J=8.4 Hz, 1H), 6.83 (d, J=8.0 Hz, 1H), 5.41 (s, 2H).

Scheme I-10 MS(ESI) (m/z): 332.1 (M+H)+. $^1$H NMR (400 MHz, DMSO-$d_6$) δ 8.54 (s, 1H), 8.17-7.98 (m, 2H), 7.89 (d, J=8.4 Hz, 1H), 7.34 (d, J=8.0 Hz, 2H), 7.29-7.17 (m, 1H), 7.09 (s, 3H), 6.99 (d, J=8.4 Hz, 1H), 6.75 (d, J=8.0 Hz, 1H), 5.28 (s, 2H), 2.24 (s, 3H).

Scheme I-11 MS(ESI) (m/z): 332.1 (M+H)+. $^1$H NMR (400 MHz, DMSO-$d_6$) δ 8.71 (d, J=2.7 Hz, 1H), 8.28 (s, 1H), 8.16 (d, J=4.6 Hz, 1H), 8.03 (d, J=8.4 Hz, 1H), 7.46 (t, J=8.2 Hz, 1H), 7.35 (q, J=5.3 Hz, 2H), 7.30 (d, J=7.7 Hz, 1H), 7.25 (t, J=7.5 Hz, 1H), 7.10 (d, J=8.1 Hz, 2H), 6.82 (d, J=8.0 Hz, 1H), 5.35 (s, 2H), 2.26 (s, 3H).

Scheme I-12 MS(ESI) (m/z): 332.1 (M+H)+. $^1$H NMR (400 MHz, DMSO-$d_6$) δ 8.73 (s, 1H), 8.27 (s, 1H), 8.17 (s, 1H), 8.05 (d, J=8.3 Hz, 1H), 7.44 (t, J=8.2 Hz, 3H), 7.37 (d, J=7.5 Hz, 1H), 7.17 (d, J=7.6 Hz, 2H), 7.10 (d, J=8.4 Hz, 1H), 6.83 (d, J=7.9 Hz, 1H), 5.36 (s, 2H), 2.25 (s, 3H).

Scheme I-13 MS(ESI) (m/z): 386.1 (M+H)+. $^1$H NMR (400 MHz, DMSO-$d_6$) δ 8.66 (d, J=2.8 Hz, 1H), 8.19 (s, 1H), 8.15 (d, J=4.6 Hz, 1H), 8.08-7.95 (m, 1H), 7.79 (d, J=7.9 Hz, 2H), 7.69 (t, J=7.7 Hz, 1H), 7.52 (dt, J=29.6, 7.9 Hz, 2H), 7.34 (dd, J=8.5, 4.7 Hz, 1H), 7.15 (d, J=8.4 Hz, 1H), 6.76 (d, J=8.0 Hz, 1H), 5.55 (s, 2H).

Scheme I-14 MS(ESI) (m/z): 386.1 (M+H)+. $^1$H NMR (400 MHz, DMSO-$d_6$) δ 8.73 (d, J=2.7 Hz, 1H), 8.37 (s, 1H), 8.19-8.12 (m, 1H), 8.08-8.01 (m, 1H), 7.97 (s, 1H), 7.82 (d, J=7.6 Hz, 1H), 7.66 (d, J=7.9 Hz, 1H), 7.60 (t, J=7.7 Hz, 1H), 7.48 (t, J=8.3 Hz, 1H), 7.34 (dd, J=8.4, 4.7 Hz, 1H), 7.12 (d, J=8.5 Hz, 1H), 6.85 (d, J=8.1 Hz, 1H), 5.48 (s, 2H).

Scheme I-15 MS(ESI) (m/z): 386.1 (M+H)+. $^1$H NMR (400 MHz, DMSO-$d_6$) δ 8.79 (d, J=2.7 Hz, 1H), 8.40 (s, 1H), 8.17 (d, J=4.7 Hz, 1H), 8.08 (d, J=8.5 Hz, 1H), 7.74 (s, 4H), 7.46 (t, J=8.2 Hz, 1H), 7.36 (dd, J=8.4, 4.8 Hz, 1H), 7.12 (d, J=8.5 Hz, 1H), 6.79 (d, J=8.1 Hz, 1H), 5.52 (s, 2H).

Scheme I-16 MS(ESI) (m/z): 348.0 (M+H)+. $^1$H NMR (400 MHz, DMSO-$d_6$) δ 8.66 (d, J=2.7 Hz, 1H), 8.18 (d, J=7.1 Hz, 2H), 8.01 (d, J=8.0 Hz, 1H), 7.53-7.43 (m, 2H), 7.39-7.30 (m, 2H), 7.10 (dd, J=19.3, 8.3 Hz, 2H), 6.94 (t, J=7.3 Hz, 1H), 6.85 (d, J=8.9 Hz, 2H), 5.38 (s, 2H), 3.81 (s, 3H).

Scheme I-17 MS(ESI) (m/z): 348.0 (M+H)+. $^1$H NMR (400 MHz, DMSO-$d_6$) δ 8.74 (d, J=2.7 Hz, 1H), 8.31 (s, 1H), 8.17 (d, J=4.7 Hz, 1H), 8.06 (d, J=8.1 Hz, 1H), 7.46 (t, J=8.2 Hz, 1H), 7.40-7.32 (m, 1H), 7.28 (d, J=7.9 Hz, 1H), 7.11 (dd, J=14.6, 6.4 Hz, 3H), 6.85 (t, J=8.9 Hz, 2H), 5.37 (s, 2H), 3.69 (s, 3H).

Scheme I-18 MS(ESI) (m/z): 348.0 (M+H)+. $^1$H NMR (400 MHz, DMSO-$d_6$) δ 8.71 (d, J=2.7 Hz, 1H), 8.22 (s, 1H), 8.17 (d, J=4.7 Hz, 1H), 8.07-8.01 (m, 1H), 7.47 (dd, J=12.7, 8.1 Hz, 3H), 7.36 (dd, J=8.4, 4.7 Hz, 1H), 7.09 (d, J=8.4 Hz, 1H), 6.92 (d, J=8.3 Hz, 2H), 6.87 (d, J=8.0 Hz, 1H), 5.32 (s, 2H), 3.70 (s, 3H).

Scheme I-19 MS(ESI) (m/z): 402.1 (M+H)+. $^1$H NMR (400 MHz, DMSO-$d_6$) δ 8.68 (d, J=2.7 Hz, 1H), 8.21 (s, 1H), 8.17 (d, J=4.7 Hz, 1H), 8.02 (d, J=7.9 Hz, 1H), 7.73 (d, J=7.6 Hz, 1H), 7.55-7.47 (m, 2H), 7.44 (d, J=7.6 Hz, 2H), 7.36 (dd, J=8.4, 4.8 Hz, 1H), 7.16 (d, J=8.4 Hz, 1H), 6.85 (d, J=8.0 Hz, 1H), 5.48 (s, 2H).

Scheme I-20 MS(ESI) (m/z): 402.0 (M+H)+. $^1$H NMR (400 MHz, DMSO-$d_6$) δ 8.75 (d, J=2.8 Hz, 1H), 8.33 (s, 1H), 8.17 (d, J=4.6 Hz, 1H), 8.09-8.01 (m, 1H), 7.57 (d, J=10.4 Hz, 2H), 7.50 (dt, J=12.3, 8.1 Hz, 2H), 7.39-7.27 (m, 2H), 7.13 (d, J=8.4 Hz, 1H), 6.86 (d, J=8.0 Hz, 1H), 5.45 (s, 2H).

Scheme I-21 MS(ESI) (m/z): 402.0 (M+H)+. $^1$H NMR (400 MHz, DMSO-$d_6$) δ 8.76 (d, J=2.7 Hz, 1H), 8.31 (s, 1H), 8.18 (d, J=4.6 Hz, 1H), 8.05 (d, J=8.5 Hz, 1H), 7.67 (d, J=8.3 Hz, 2H), 7.48 (t, J=8.2 Hz, 1H), 7.38 (d, J=8.1 Hz, 3H), 7.12 (d, J=8.4 Hz, 1H), 6.84 (d, J=7.9 Hz, 1H), 5.44 (s, 2H).

Scheme I-22 MS(ESI) (m/z): 343.1 (M+H)+. $^1$H NMR (400 MHz, DMSO-$d_6$) δ 8.71 (d, J=2.6 Hz, 1H), 8.17 (d, J=4.7 Hz, 2H), 8.04 (ddd, J=8.3, 2.8, 1.4 Hz, 1H), 7.96-7.88 (m, 1H), 7.83 (d, J=7.8 Hz, 1H), 7.79-7.71 (m, 1H), 7.61-7.47 (m, 2H), 7.36 (dd, J=8.4, 4.7 Hz, 1H), 7.17 (d, J=8.4 Hz, 1H), 6.95 (d, J=8.0 Hz, 1H), 5.60 (s, 2H).

Scheme I-23 MS(ESI) (m/z): 343.1 (M+H)+. $^1$H NMR (400 MHz, DMSO-$d_6$) δ 8.74 (s, 1H), 8.33 (s, 1H), 8.14 (d, J=4.6 Hz, 1H), 8.04 (d, J=5.3 Hz, 2H), 7.85 (d, J=7.9 Hz, 1H), 7.76 (d, J=7.6 Hz, 1H), 7.58 (d, J=7.7 Hz, 1H), 7.45 (t, J=8.2 Hz, 1H), 7.39-7.29 (m, 1H), 7.11 (d, J=8.4 Hz, 1H), 6.80 (d, J=8.0 Hz, 1H), 5.42 (s, 2H).

Scheme I-24 MS(ESI) (m/z): 343.1 (M+H)+. $^1$H NMR (400 MHz, DMSO-$d_6$) δ 8.78 (s, 1H), 8.37 (s, 1H), 8.21-8.10 (m, 1H), 8.06 (d, J=8.4 Hz, 1H), 7.83 (d, J=7.8 Hz, 2H), 7.69 (d, J=7.9 Hz, 2H), 7.44 (t, J=8.2 Hz, 1H), 7.35 (t, J=6.7 Hz, 1H), 7.11 (d, J=8.4 Hz, 1H), 6.76 (d, J=8.0 Hz, 1H), 5.49 (s, 2H).

Scheme I-25 MS(ESI) (m/z): 346.1 (M+H)+. $^1$H NMR (400 MHz, DMSO-$d_6$) δ 8.27 (d, J=2.7 Hz, 1H), 8.11 (d, J=4.6 Hz, 1H), 7.79 (d, J=5.5 Hz, 2H), 7.56 (t, J=8.2 Hz, 1H), 7.29 (dd, J=8.5, 4.7 Hz, 1H), 7.16 (dd, J=7.8, 5.8 Hz, 2H), 7.08 (d, J=7.5 Hz, 2H), 7.01 (d, J=8.0 Hz, 1H), 5.34 (s, 2H), 2.36 (s, 6H).

Scheme I-26 MS(ESI) (m/z): 386.0 (M+H)+. $^1$H NMR (400 MHz, DMSO-$d_6$) δ 8.46 (d, J=2.7 Hz, 1H), 8.15 (d, J=4.7 Hz, 1H), 7.94 (s, 1H), 7.89 (d, J=9.5 Hz, 1H), 7.60 (d, J=7.6 Hz, 3H), 7.50 (dd, J=8.9, 7.2 Hz, 1H), 7.34 (dd, J=8.4, 4.6 Hz, 1H), 7.23 (d, J=8.4 Hz, 1H), 7.13 (d, J=8.0 Hz, 1H), 5.54 (s, 2H).

Scheme I-27 MS(ESI) (m/z): 354.1 (M+H)+. $^1$H NMR (400 MHz, DMSO-$d_6$) δ 8.60 (s, 1H), 8.19 (d, J=4.3 Hz, 1H), 8.11 (s, 1H), 7.97 (d, J=8.2 Hz, 1H), 7.66-7.48 (m, 2H), 7.37 (dd, J=8.3, 4.4 Hz, 1H), 7.26-7.14 (m, 3H), 7.07 (d, J=7.9 Hz, 1H), 5.49 (s, 2H).

Application Case 3: Synthesis of 4-((5-chloro-2-(trifluoromethoxy)benzyl)oxy)-N-(pyridin-3-yl)benzo[d]isoxazol-3-amine (Scheme I-3)

1. Synthesis of 5-chloro-2-(trifluoromethoxy)benzaldehyde (Compound 13)

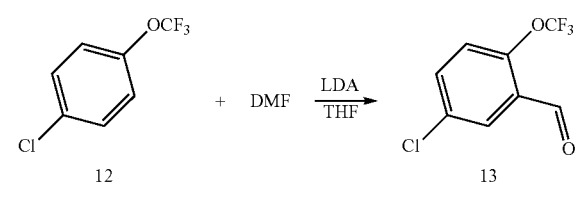

Dissolve 1.0 g 1-chloro-4-(trifluoromethoxy)benzene (5.1 mmol, 1.0 eq) in 20 mL anhydrous tetrahydrofuran, protect with nitrogen, cool to −80° C., and add 3.1 mL 2M LDA (6.1 mmol, 1.2 eq) dropwise. After 15 minutes of dripping, keep at −80° C. for 20 min, add 0.47 mL DMF, slowly warm to −50° C. for 40 min, add 1.22 g acetic acid (20.4 mmol, 4.0 eq) to quench the reaction. Then water was added to the residue and extracted with EA, the organic layers washed with saturated sodium chloride solution, dried over $Na_2SO_4$, filtered, and concentrated. The residue was purified with column chromatography (PE/EA=20:1) to give compound 13, 800 mg light yellow oily substance, yield 70%.

The structure is confirmed correct and data are as follow: MS (ESI) (m/z): 225.0 (M+H)$^+$. $^1$H NMR (400 MHz, DMSO-d$_6$) δ 10.14 (s, 1H), 7.91 (d, J=2.7 Hz, 1H), 7.88 (dd, J=8.8, 2.6 Hz, 1H), 7.60 (dd, J=8.8, 1.7 Hz, 1H).

2. Synthesis of 5-chloro-2-(trifluoromethoxy)phenyl)methanol (Compound 14)

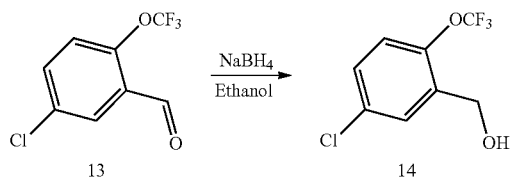 [SMILES: O=Cc1cc(Cl)ccc1OC(F)(F)F ; "NaBH4" ; OCc1cc(Cl)ccc1OC(F)(F)F]

Add 800 mg 5-chloro-2-(trifluoromethoxy)benzaldehyde (3.57 mmol, 1.0 eq) and 10 mL ethanol to the reaction flask, and add 160 mg NaBH$_4$ (4.21 mmol, 1.2 eq) to the above system under an ice bath. Then, the reaction was stirred for 30 min in an ice bath, and then raised to room temperature and reacted for 3 h. After the most of the solution was removed under reduced pressure, water was added to the residue and extracted with EA, the organic layers washed with saturated sodium chloride solution, dried over $Na_2SO_4$, filtered, and concentrated. The residue was purified with column chromatography (PE/EA=15:1) to give compound 14, 600 mg white solid, yield 75%.

The structure is confirmed correct and data are as follow: MS (ESI) (m/z): 225.0 (M+H)$^+$. $^1$H NMR (400 MHz, DMSO-d$_6$) δ 7.56 (d, J=2.6 Hz, 1H), 7.42 (dd, J=8.8, 2.6 Hz, 1H), 7.33 (dd, J=8.7, 1.6 Hz, 1H), 5.49 (t, J=5.8 Hz, 1H), 4.52 (d, J=5.9 Hz, 2H).

3. Synthesis of 4-((5-chloro-2-(trifluoromethoxy)benzyl)oxy)-N-(pyridin-3-yl)benzo[d]isoxazol-3-amine (Scheme I-3)

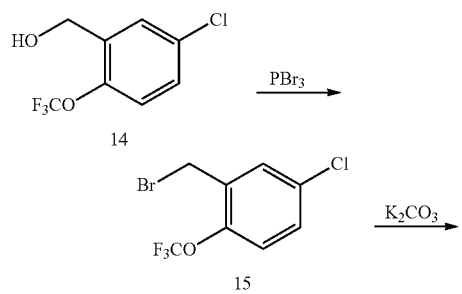

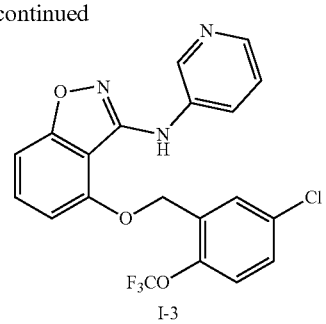

With reference to the conditions of the fifth and six-step synthesis of Scheme I-1 in application case 1, the substituted benzyl alcohol was used to prepare substituted benzyl bromide, substituted benzyl bromide and 3-(Pyridin-3-ylamino)benzo[d]isoxazol-4-ol reaction yields the corresponding target compound.

The structure is confirmed correct and data are as follow: Scheme I-3 MS(ESI) (m/z): 436.1 (M+H)$^+$. $^1$H NMR (400 MHz, DMSO-d$_6$) δ 8.68 (s, 1H), 8.29 (s, 1H), 8.12 (d, J=4.5 Hz, 1H), 8.00 (d, J=8.3 Hz, 1H), 7.84 (s, 1H), 7.53-7.44 (m, 3H), 7.35-7.30 (m, 1H), 7.14 (d, J=8.4 Hz, 1H), 6.84 (d, J=8.0 Hz, 1H), 5.39 (s, 2H).

Application Case 4: Synthesis of 4-((2,6-dichlorobenzyl)oxy)-N-methyl-N-(pyridin-3-yl)benzo[d]isoxazol-3-amine (Scheme I-28)

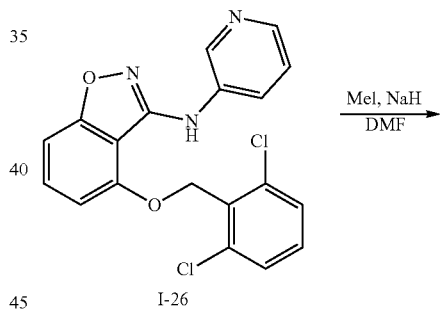

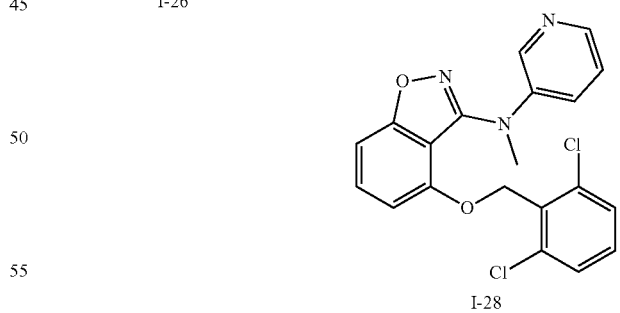

Add 40 mg I-26 (0.10 mmol, 1.0 eq) and 5 mL DMF to the flask, add 5 mg sodium hydride (0.14 mmol, 1.3 eq) to the system under ice bath, then add 15 mg methyl iodide (0.104 mmol, 1.0 eq). After stirring the reaction for 15 min in an ice bath, and then raised to room temperature and reacted for 1 h, After the reaction was complete, water was added to the residue and extracted with EA, the organic layers washed with saturated sodium chloride solution, dried over $Na_2SO_4$, filtered, and concentrated. The residue was purified with column chromatography (PE/EA=3:1) to give compound I-28, 20 mg white solid, yield 50%.

The structure was confirmed correct and data are as follow: MS (ESI) (m/z): 401.0 (M+H)⁺. $^1$H NMR (400 MHz, DMSO-d6) δ 7.92 (d, J=2.7 Hz, 1H), 7.86-7.78 (m, 1H), 7.55 (t, J=8.2 Hz, 1H), 7.44 (d, J=3.3 Hz, 3H), 7.24 (d, J=8.5 Hz, 1H), 7.07 (ddd, J=8.2, 3.0, 1.4 Hz, 1H), 6.91 (d, J=8.0 Hz, 1H), 6.69 (dd, J=8.3, 4.7 Hz, 1H), 4.95 (s, 2H), 3.26 (s, 3H).

Application Case 5: Synthesis of 4-(benzyloxy)-N-(pyridin-3-yl)-1H-indazol-3-amine (Scheme I-29)

1. Synthesis of 4-(benzyloxy)-1H-indazol-3-amine (Compound 16)

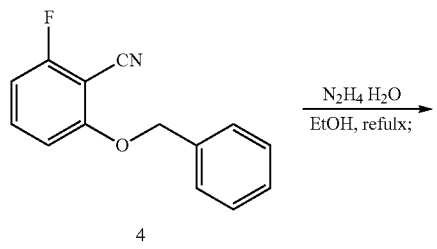

Add 1.0 g 4 (4.4 mmol, 1.0 eq) and 4 mL 85% hydrazine hydrate, 10 mL ethanol to the reaction flask, and raise the temperature to 100° C. to react overnight. After the reaction is complete, evaporate the solvent, add 5 mL water and stir to obtain a suspension. The suspension was filtered to obtain compound 16, 840 mg white solid, yield 80%.

The structure is confirmed correct and data are as follow: MS(ESI) (m/z): 240.0 (M+H)⁺. $^1$H NMR (400 MHz, DMSO-d₆) δ 11.39 (s, 1H), 7.47 (d, J=7.5 Hz, 2H), 7.37 (t, J=7.5 Hz, 2H), 7.29 (t, J=7.3 Hz, 1H), 7.04 (t, J=8.0 Hz, 1H), 6.73 (d, J=8.3 Hz, 1H), 6.35 (d, J=7.7 Hz, 1H), 5.17 (s, 2H), 4.90 (s, 2H).

2. Synthesis of 2-(4-(benzyloxy)-1H-indazol-3-yl)isoindoline-1,3-dione (Compound 17)

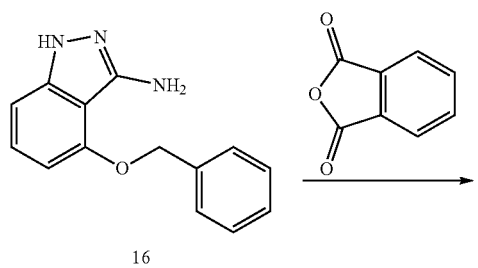

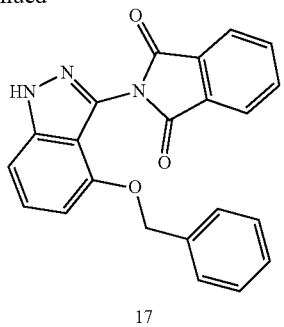

Add 240 mg 15 (1.0 mmol, 1.0 eq) and 148 mg phthalic anhydride (1.0 mmol, 1.0 eq) to the reaction flask, raise the temperature to 170° C. and react for 30 minutes. After the reaction is complete, cool to room temperature and add 5 mL EA, and then stirred to obtain a suspension, and filtered to obtain compound 17, 185 mg white solid, yield 50%.

The structure is confirmed correct and data are as follow: MS(ESI) (m/z): 370.0 (M+H)⁺. $^1$H NMR (400 MHz, DMSO-d₆) δ 13.46 (s, 1H), 7.93-7.83 (m, 4H), 7.32 (t, J=8.0 Hz, 1H), 7.15 (d, J=8.4 Hz, 1H), 7.08-6.97 (m, 3H), 6.92 (t, J=7.6 Hz, 2H), 6.65 (d, J=7.7 Hz, 1H), 4.96 (s, 2H).

3. Synthesis of tert-butyl 4-(benzyloxy)-3-(1,3-dioxoisoindolin-2-yl)-1H-indazole-1-carboxylate (Compound 18)

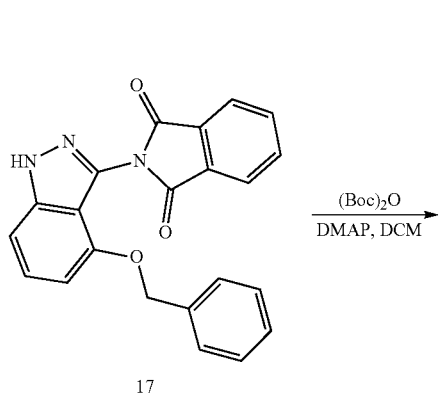

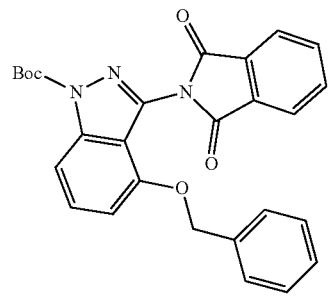

Add 200 mg 17 (0.54 mmol, 1.0 eq) and 198 mg DMAP (1.63 mmol, 3.0 eq) to the reaction flask, then dissolve in 5 mL DCM, and then add 142 mg (Boc)₂O (0.65 mmol, 1.2 eq). After reacting at room temperature overnight, add water, extracted with DCM, the organic layers washed with saturated sodium chloride solution, dried over Na₂SO₄, filtered, and concentrated. The residue was purified with column chromatography (PE/EA=6:1) to give compound 18, 80 mg white solid, yield 31%.

The structure is confirmed correct and data are as follow: MS(ESI) (m/z): 470.0 (M+H)+. ¹H NMR (400 MHz, DMSO-d₆) δ 7.85 (s, 4H), 7.71 (d, J=8.5 Hz, 1H), 7.61 (t, J=8.2 Hz, 1H), 7.04 (t, J=7.2 Hz, 1H), 7.02-6.96 (m, 3H), 6.94 (t, J=7.5 Hz, 2H), 4.99 (s, 2H), 1.63 (s, 9H).

4. Synthesis of tert-butyl 3-amino-4-(benzyloxy)-1H-indazole-1-carboxylate (Compound 19)

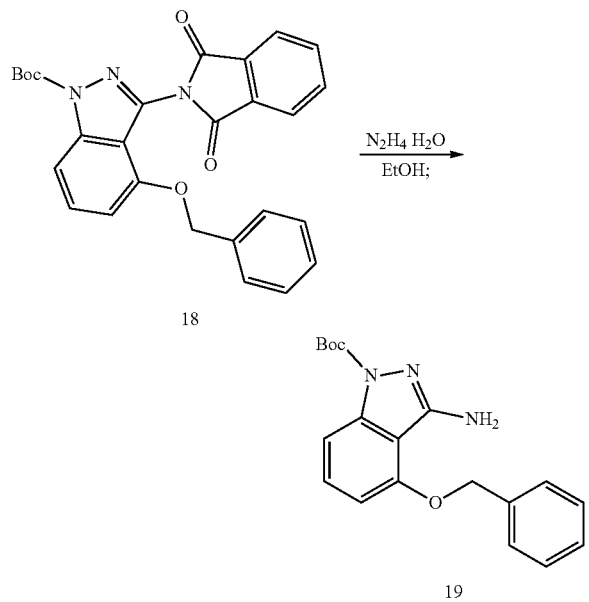

Add 50 mg 18 (0.11 mmol, 1.0 eq) and 6.9 mg 85% hydrazine hydrate (0.14 mmol, 1.4 eq), 3 mL ethanol to the reaction flask, and react at room temperature for 5 h. After the reaction is complete, evaporate the solvent, add water, extracted with DCM, the organic layers washed with saturated sodium chloride solution, dried over Na₂SO₄, filtered, and concentrated. The residue was purified with column chromatography (PE/EA=4:1) to give compound 19, 20 mg white solid, yield 56%.

The structure is confirmed correct and data are as follow: MS (ESI): m/z 340[M+H]+. ¹H NMR (400 MHz, DMSO-d₆) δ 7.51-7.42 (m, 3H), 7.40-7.32 (m, 3H), 7.33-7.27 (m, 1H), 6.78 (d, J=7.9 Hz, 1H), 5.81 (s, 2H), 5.26 (s, 2H), 1.52 (s, 9H).

5. Synthesis of tert-butyl 4-(benzyloxy)-3-(pyridin-3-ylamino)-1H-indazole-1-carboxylate (Compound 20)

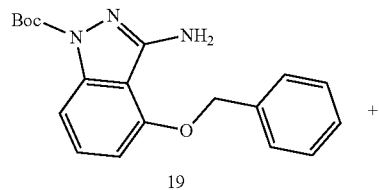 +

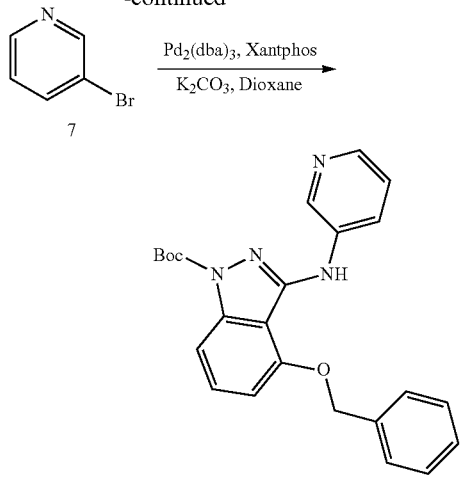

According to the conditions for synthesizing compound 8 in the third step in application case 1, the corresponding amino compound 19 is reacted with 3-bromopyridine (compound 7) to obtain the corresponding target compound 20.

The structure is confirmed correct and data are as follow: MS (ESI): m/z 417[M+H]+. ¹H NMR (400 MHz, DMSO-d₆) δ 8.74 (s, 1H), 8.18 (s, 1H), 8.15 (d, J=2.4 Hz, 1H), 8.14-8.10 (m, 1H), 7.55 (d, J=7.5 Hz, 2H), 7.52-7.43 (m, 2H), 7.40 (t, J=7.5 Hz, 2H), 7.37-7.29 (m, 2H), 6.89 (d, J=7.5 Hz, 1H), 5.40 (s, 2H), 1.59 (s, 9H).

6. Synthesis of 4-(benzyloxy)-N-(pyridin-3-yl)-1H-indazol-3-amine (Scheme I-29)

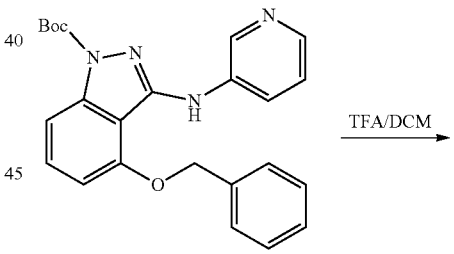

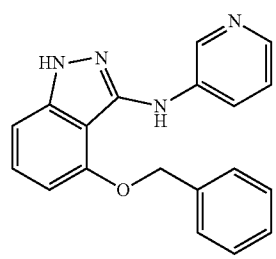

I-29

Add 50 mg 20 (0.12 mmol, 1.0 eq) to the reaction flask, dissolve in 5 mL dichloromethane, add 0.3 mL trifluoroacetic acid, react at room temperature for 2 h, after the reaction is complete, add water, extracted with DCM, the organic layers washed with saturated sodium chloride solution, dried over Na₂SO₄, filtered, and concentrated. The residue was purified with column chromatography (PE/EA=3:1) to give compound I-29, 20 mg white solid, yield 53%.

The structure is confirmed correct and data are as follow: MS (ESI): m/z 317[M+H]+. 1H NMR (400 MHz, DMSO-d6) δ 12.16 (s, 1H), 8.54 (d, J=2.7 Hz, 1H), 7.98 (d, J=4.6 Hz, 1H), 7.96-7.91 (m, 1H), 7.86 (s, 1H), 7.48 (d, J=7.4 Hz, 2H), 7.36 (t, J=7.4 Hz, 2H), 7.30 (d, J=7.1 Hz, 1H), 7.23 (dd, J=8.4, 4.7 Hz, 1H), 7.16 (t, J=8.0 Hz, 1H), 6.89 (d, J=8.3 Hz, 1H), 6.49 (d, J=7.7 Hz, 1H), 5.27 (s, 2H).

Application Case 6: Synthesis of 4-(benzyloxy)-1-methyl-N-(pyridin-3-yl)-1H-indazol-3-amine (Scheme I-30)

1. Synthesis of 2-(4-(benzyloxy)-1-methyl-1H-indazol-3-yl)isoindoline-1,3-dione (Compound 21)

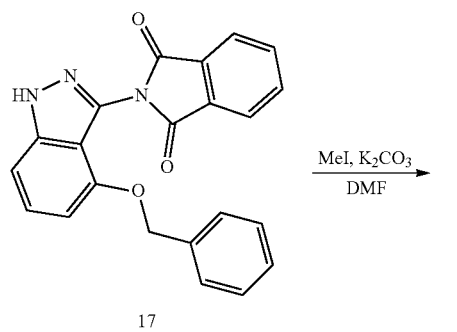

17

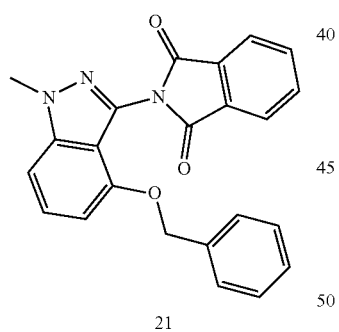

21

Add 150 mg 17 (0.41 mmol, 1.0 eq) and 112 mg K2CO3 (0.81 mmol, 2.0 eq) to the reaction flask, dissolve in 5 mL DMF, then add 75 mg methyl iodide (0.53 mmol, 1.3 eq) at room temperature. After overnight reaction, add water, extracted with DCM, the organic layers washed with saturated sodium chloride solution, dried over Na2SO4, filtered, and concentrated. The residue was purified with column chromatography (PE/EA=4:1) to give compound 21, 100 mg white solid, yield 64%.

The structure is confirmed correct and data are as follow: MS (ESI): m/z 384[M+H]+. 1H NMR (400 MHz, DMSO-d6) δ 7.77 (t, J=1.8 Hz, 4H), 7.31-7.23 (m, 1H), 7.16 (dd, J=8.6, 1.8 Hz, 1H), 6.95-6.86 (m, 3H), 6.86-6.77 (m, 2H), 6.58 (dd, J=7.6, 1.7 Hz, 1H), 4.86 (s, 2H), 3.94 (s, 3H).

2. Synthesis of 4-(benzyloxy)-1-methyl-N-(pyridin-3-yl)-1H-indazol-3-amine (Scheme I-30)

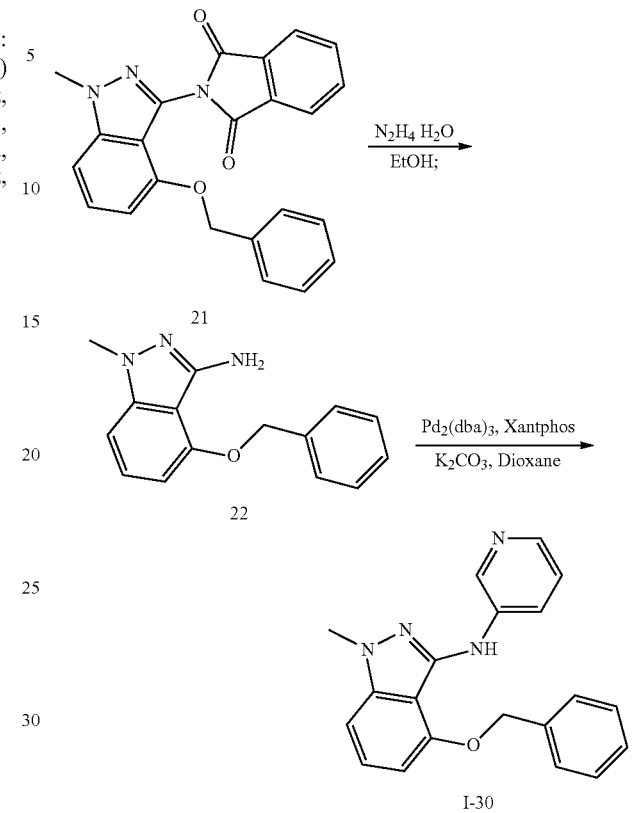

According to the conditions for synthesizing compound 20 in the third and fourth steps in application case 5, the corresponding compound 21 is used in place of compound 18 to carry out the corresponding similar reaction to obtain the corresponding target compound I-30.

The structure is confirmed correct and data are as follow: MS (ESI): m/z 311[M+H]+. 1H NMR (400 MHz, DMSO-d6) δ 8.56 (d, J=2.7 Hz, 1H), 8.00 (d, J=4.7 Hz, 1H), 7.95 (dt, J=8.5, 2.0 Hz, 1H), 7.90 (s, 1H), 7.47 (d, J=7.4 Hz, 2H), 7.36 (t, J=7.4 Hz, 2H), 7.30 (d, J=7.2 Hz, 1H), 7.27-7.17 (m, 2H), 7.00 (d, J=8.4 Hz, 1H), 6.51 (d, J=7.7 Hz, 1H), 5.29 (s, 2H), 3.84 (s, 3H).

Application Case 7: Synthesis of 4-(benzyloxy)-N-(pyridin-3-yl)benzo[d]isothiazol-3-amine (Scheme I-31)

1. Synthesis of 4-(benzyloxy)benzo[d]isothiazol-3-amine (Compound 23)

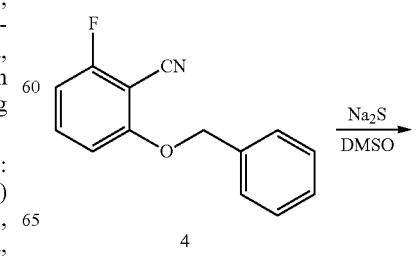

4

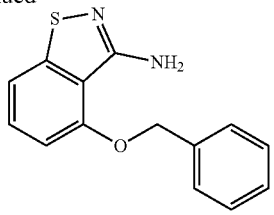

23

Add 228 mg 4 (1.0 mmol, 1.0 eq) and 78 mg sodium sulfide (1.0 mmol, 1.0 eq) to the reaction flask, dissolve it in 5 mL DMSO under nitrogen, and react at 70° C. for 12 h. Then the whole reaction system was cooled to 0° C., 1.4 mL 25% aqueous ammonia solution and 1.4 mL of 15% sodium hypochlorite solution were added dropwise. The reaction was slowly warmed to room temperature and reacted for 5 h. After the reaction is complete, add water, extracted with EA, the organic layers washed with saturated sodium chloride solution, dried over $Na_2SO_4$, filtered, and concentrated. The residue was purified with column chromatography (PE/EA=4:1) to give compound 23, 200 mg white solid, yield 78%.

The structure is confirmed correct and data are as follow: MS (ESI): m/z 257 [M+H]$^+$. $^1$H NMR (400 MHz, DMSO-d$_6$) δ 7.50 (s, 1H), 7.48 (s, 1H), 7.42-7.32 (m, 4H), 7.36-7.27 (m, 1H), 6.89 (d, J=7.4 Hz, 1H), 6.45 (s, 2H), 5.28 (s, 2H).

2. Synthesis of 4-(benzyloxy)-N-(pyridin-3-yl)benzo[d]isothiazol-3-amine (Scheme I-31)

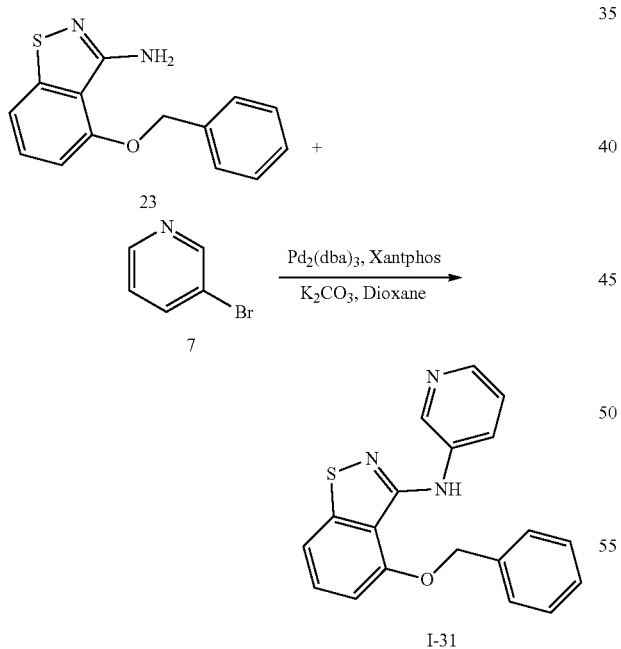

According to the conditions for synthesizing compound 8 in the third step in application case 1, the corresponding amino compound 23 is reacted with 3-bromopyridine (compound 7) to obtain the corresponding target compound I-31.

The structure is confirmed correct and data are as follow: MS (ESI): m/z 334 [M+H]$^+$. $^1$H NMR (400 MHz, DMSO-d$_6$) δ 9.03 (s, 1H), 8.44 (d, J=2.7 Hz, 1H), 8.23 (dd, J=8.6, 1.8 Hz, 1H), 8.12 (dd, J=4.7, 1.8 Hz, 1H), 7.62 (d, J=7.2 Hz, 2H), 7.58 (d, J=8.1 Hz, 1H), 7.53-7.38 (m, 4H), 7.30 (dd, J=8.6, 4.7 Hz, 1H), 7.07 (d, J=7.8 Hz, 1H), 5.42 (s, 2H).

Application Case 8: Synthesis of 8-(benzyloxy)-N-(pyridin-3-yl)isoquinolin-1-amine (Scheme I-32)

1. Synthesis of 8-(benzyloxy)isoquinoline (Compound 25)

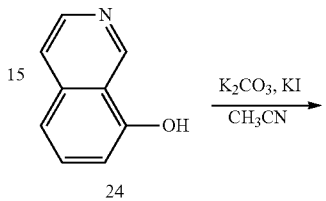

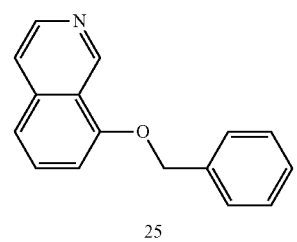

Referring to the conditions for synthesizing compound 2 in the first step in application case 1, the corresponding hydroxy compound 24 is reacted with benzyl bromide to obtain the corresponding target compound 25.

The structure is confirmed correct and data are as follow: MS (ESI): m/z 236[M+H]$^+$. $^1$H NMR (400 MHz, DMSO-d$_6$) δ 10.70 (s, 1H), 7.48 (d, J=7.6 Hz, 2H), 7.39 (t, J=8.0 Hz, 1H), 7.24 (t, J=7.5 Hz, 2H), 7.14 (t, J=7.3 Hz, 1H), 6.99 (d, J=7.9 Hz, 1H), 6.94 (t, J=6.5 Hz, 1H), 6.87 (d, J=8.1 Hz, 1H), 6.25 (d, J=7.0 Hz, 1H), 5.07 (s, 2H).

2. Synthesis of 8-(benzyloxy)isoquinoline 2-oxide (compound 26)

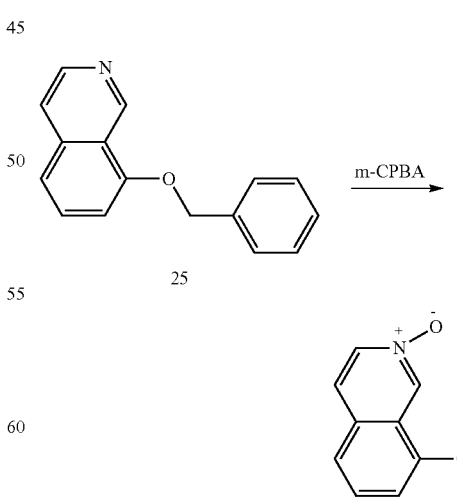

Add 290 mg 26 (1.23 mmol, 1.0 eq) and 225 mg m-chloroperoxybenzoic acid (m-CPBA) (1.48 mmol, 1.2 eq) to the reaction flask, dissolve in 5 mL DCM, and react at room temperature for 12 h. Quench the reaction with saturated aqueous sodium carbonate, add water, extracted with EA, the organic layers washed with saturated sodium chloride solution, dried over $Na_2SO_4$, filtered, and concentrated. The residue was purified with column chromatography (PE/EA=1:1) to give compound 26, 260 mg white solid, yield 84%.

The structure is confirmed correct and data are as follow: MS (ESI): m/z 252[M+H]$^+$. $^1$H NMR (400 MHz, DMSO-d$_6$) δ 8.61 (t, J=1.2 Hz, 1H), 8.02 (dd, J=7.1, 1.8 Hz, 1H), 7.76 (d, J=7.1 Hz, 1H), 7.43-7.34 (m, 4H), 7.28 (t, J=7.4 Hz, 2H), 7.21 (t, J=7.2 Hz, 1H), 7.12-7.06 (m, 1H), 5.18 (s, 2H).

3. Synthesis of 8-(benzyloxy)-1-chloroisoquinoline (Compound 27)

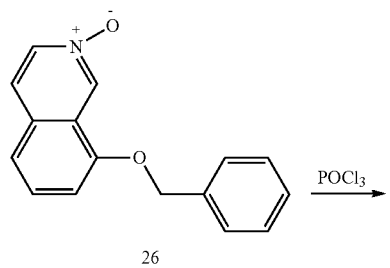

Add 200 mg 26 (0.80 mmol, 1.0 eq) and 1.5 mL phosphorus oxychloride (POCl$_3$) to the reaction flask, and react at 90° C. for 5 h. After the reaction was completed, most of the solvent was distilled off under reduced pressure, water was added, the pH was adjusted to 8-9 with saturated sodium carbonate aqueous solution, extracted with DCM, the organic layers washed with saturated sodium chloride solution, dried over $Na_2SO_4$, filtered, and concentrated to give compound 27. Without further purification, it was directly used in the next reaction.

4. Synthesis of 8-(benzyloxy)-N-(pyridin-3-yl)isoquinolin-1-amine (Scheme I-32)

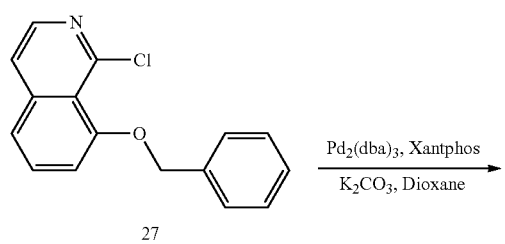

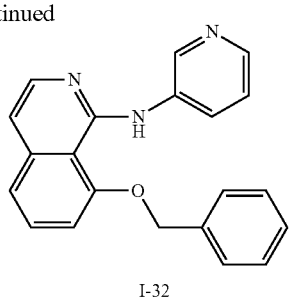

Referring to the conditions for synthesizing compound 8 in the third step in application case 1, the corresponding compound 27 is reacted with 3-aminopyridine to obtain the corresponding target compound I-32.

The structure is confirmed correct and data are as follow: MS (ESI): m/z 328[M+H]$^+$. $^1$H NMR (400 MHz, DMSO-d$_6$) δ 10.01 (s, 1H), 8.19 (d, J=2.6 Hz, 1H), 8.14 (dd, J=8.6, 2.4 Hz, 1H), 8.08 (d, J=4.0 Hz, 1H), 7.97 (d, J=5.7 Hz, 1H), 7.72-7.64 (m, 2H), 7.63 (t, J=8.0 Hz, 1H), 7.54-7.45 (m, 3H), 7.40 (d, J=8.0 Hz, 1H), 7.27 (d, J=7.8 Hz, 1H), 7.23 (dd, J=8.3, 4.7 Hz, 1H), 7.13 (d, J=5.7 Hz, 1H), 5.40 (s, 2H).

Application Case 9: Synthesis of 4-((2-chloro-5-fluorobenzyl)oxy)-N-(pyrimidin-5-yl)benzo[d]isoxazol-3-amine (Scheme I-33)

1. Synthesis of 2-((2-chloro-5-fluorobenzyl)oxy)-6-fluorobenzonitrile (Compound 29)

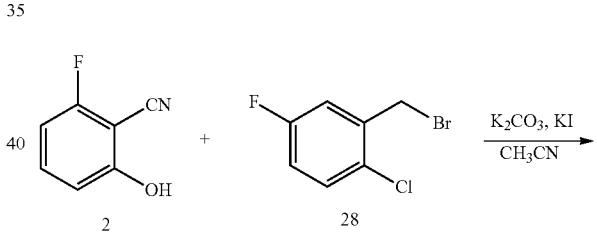

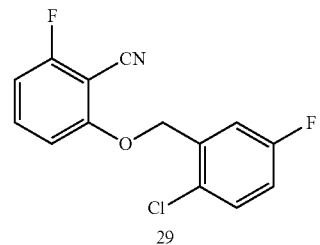

Referring to the conditions of the first step in application case 1 to synthesize compound 4, the corresponding compound 2 and 28 are reacted to obtain the corresponding target compound 29.

The structure is confirmed correct and data are as follow: MS (ESI): m/z 280 [M+H]$^+$. $^1$H NMR (400 MHz, DMSO-d$_6$) δ 7.77-7.66 (m, 1H), 7.57 (dd, J=8.9, 5.1 Hz, 1H), 7.47 (dd, J=9.2, 3.1 Hz, 1H), 7.33-7.24 (m, 1H), 7.22 (d, J=8.6 Hz, 1H), 7.08 (t, J=8.8 Hz, 1H), 5.30 (s, 2H).

2. Synthesis of 4-((2-chloro-5-fluorobenzyl)oxy)benzo[d]isoxazol-3-amine (Compound 30)

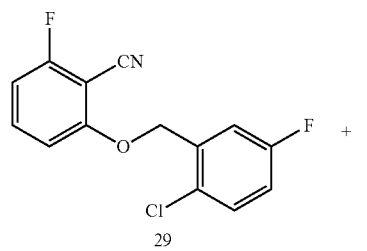

29

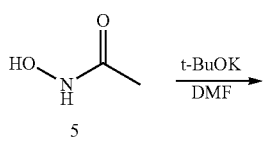

5

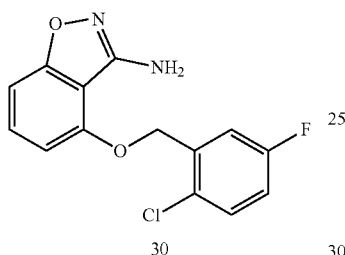

30

Referring to the conditions for synthesizing compound 6 in the second step in application case 1, the corresponding compound 29 is reacted with 5 to obtain the corresponding target compound 30.

The structure is confirmed correct and data are as follow: MS (ESI): m/z 293[M+H]$^+$. $^1$H NMR (400 MHz, DMSO-d$_6$) δ 7.60-7.52 (m, 1H), 7.53-7.44 (m, 1H), 7.43-7.34 (m, 1H), 7.31-7.21 (m, 1H), 7.03-6.96 (m, 1H), 6.74 (d, J=8.0 Hz, 1H), 5.85 (s, 2H), 5.30 (s, 2H).

3. Synthesis of 4-((2-chloro-5-fluorobenzyl)oxy)-N-(pyrimidin-5-yl)benzo[d]isoxazol-3-amine (Scheme I-33)

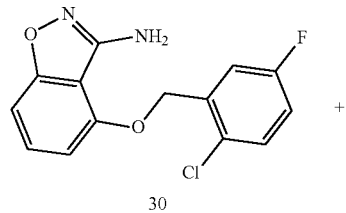

30

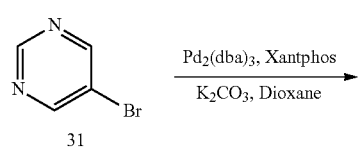

31

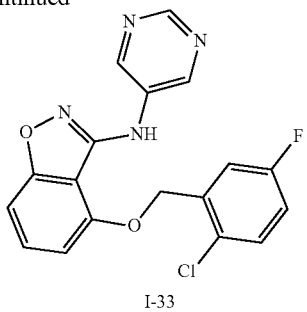

I-33

Referring to the conditions for synthesizing compound 8 in the third step in application case 1, the corresponding compounds 30 and 31 are reacted to obtain the corresponding target compound I-33.

Application Case 10: Synthesis of N-(4-((2-chloro-5-fluorobenzyl)oxy)benzo[d]isoxazol-3-yl)-2-(dimethylamino) acetamide (Scheme I-34)

1. Synthesis of 2-chloro-N-(4-((2-chloro-5-fluorobenzyl)oxy)benzo[d]isoxazol-3-yl)acetamide (Compound 33)

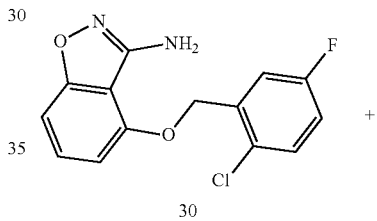

30

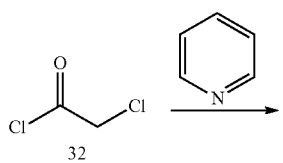

32

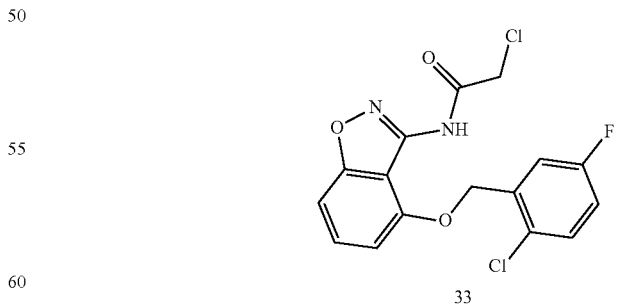

33

Add 200 mg 30 (0.68 mmol, 1.0 eq) and 108 mg pyridine (1.36 mmol, 2.0 eq) to the reaction flask, dissolve in 10 mL DCM, then slowly add 116 mg chloroacetyl chloride (1.02 mmol, 1.5 eq). React at room temperature for 2 h. Then add water, extracted with DCM, the organic layers washed with saturated sodium chloride solution, dried over Na₂SO₄, filtered, and concentrated. The residue was purified with column chromatography (PE/EA=2:1) to give compound 33, 130 mg white solid, yield 52%.

The structure is confirmed correct and data are as follow: MS (ESI): m/z 370[M+H]⁺. ¹H NMR (400 MHz, DMSO-d₆) δ 10.53 (s, 1H), 7.62-7.52 (m, 2H), 7.48 (dd, J=9.4, 3.0 Hz, 1H), 7.29 (d, J=8.5 Hz, 1H), 7.25 (dd, J=8.5, 3.0 Hz, 1H), 6.91 (d, J=8.0 Hz, 1H), 5.28 (s, 2H), 4.22 (s, 2H).

2. Synthesis of N-(4-((2-chloro-5-fluorobenzyl)oxy) benzo[d]isoxazol-3-yl)-2-(dimethylamino)acetamide (Scheme I-34)

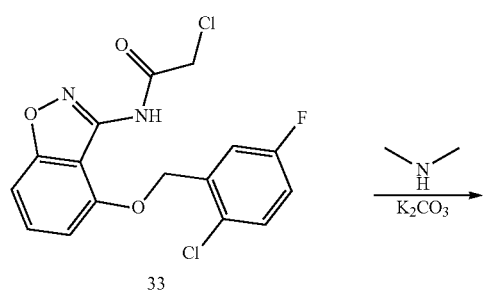

Add 70 mg 33 (0.19 mmol, 1.0 eq) and 2 mL of 2M dimethylamine (4 mmol, 20.0 eq) in tetrahydrofuran to the reaction flask, dissolve in 5 mL acetonitrile, then add 66 mg potassium carbonate (0.48 mmol, 2.5 eq) and 15 mg potassium iodide, heated to 45° C. for 2 h. Add water, extracted with EA, the organic layers washed with saturated sodium chloride solution, dried over Na₂SO₄, filtered, and concentrated. The residue was purified with column chromatography (PE/EA=1:1) to give compound I-34, 29 mg white solid, 40% yield.

The structure is confirmed correct and data are as follow: MS (ESI): m/z 378[M+H]⁺. ¹H NMR (400 MHz, DMSO-d₆) δ 10.10 (s, 1H), 7.67-7.57 (m, 3H), 7.40-7.31 (m, 1H), 7.28 (d, J=8.4 Hz, 1H), 7.03 (d, J=8.0 Hz, 1H), 5.31 (s, 2H), 3.00 (s, 2H), 1.96 (s, 6H).

Application Case 11: Synthesis of I-35~I-38

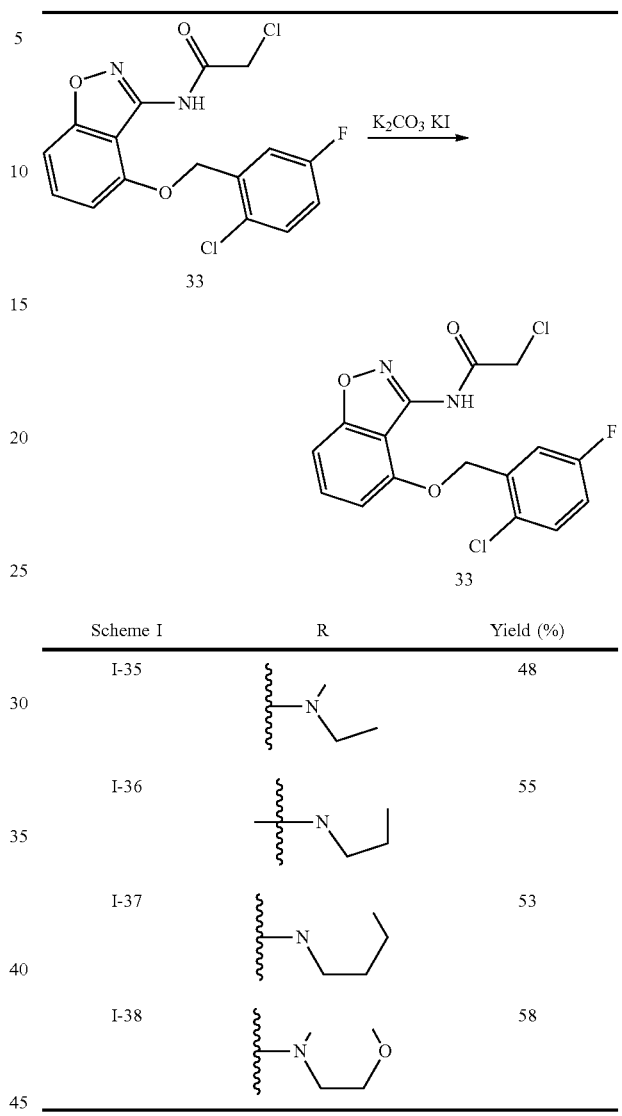

According to the conditions for synthesizing the compound formula I-34 in the second step in application case 10, the corresponding alkylamine is reacted with the intermediate 31 to obtain the corresponding target compounds formula I-35 to I-38, that is:

N-(4-((2-chloro-5-fluorobenzyl)oxy)benzo[d]isoxazol-3-yl)-2-(diethylamino) acetamide (scheme I-35);
N-(4-((2-chloro-5-fluorobenzyl)oxy)benzo[d]isoxazol-3-yl)-2-(pyrrolidin-1-y) acetamide (scheme I-36);
N-(4-((2-chloro-5-fluorobenzyl)oxy)benzo[d]isoxazol-3-yl)-2-(piperidin-1-yl)acetamide (scheme I-37);
N-(4-((2-chloro-5-fluorobenzyl)oxy)benzo[d]isoxazol-3-yl)-2-morpholinoacetamide (scheme I-38).

The structures were confirmed correct and data are as follow:

Scheme I-35 MS(ESI) (m/z): 406.1 (M+H)⁺. ¹H NMR (400 MHz, DMSO-d₆) δ 10.18 (s, 1H), 7.71-7.52 (m, 3H), 7.39-7.28 (m, 1H), 7.24 (d, J=8.4 Hz, 1H), 7.02 (d, J=8.1 Hz, 1H), 5.29 (s, 2H), 3.00 (s, 2H), 2.11 (q, J=7.2 Hz, 4H), 0.74 (t, J=7.2 Hz, 6H).

Scheme I-36 MS(ESI) (m/z): 404.1 (M+H)⁺. ¹H NMR (400 MHz, DMSO-d₆) δ 10.10 (s, 1H), 7.57-7.51 (m, 3H), 7.25 (q, J=8.6 Hz, 2H), 6.92 (d, J=8.0 Hz, 1H), 5.30 (s, 2H), 3.16 (s, 2H), 2.38 (s, 4H), 1.47 (s, 4H).

Scheme I-37 MS(ESI) (m/z): 418 (M+H)⁺. ¹H NMR (400 MHz, DMSO-d₆) δ 10.11 (s, 1H), 7.61-7.53 (m, 2H), 7.53-7.46 (m, 1H), 7.33-7.20 (m, 2H), 6.92 (d, J=8.1 Hz, 1H), 5.37 (s, 2H), 3.02 (s, 2H), 2.29 (s, 4H), 1.37-1.20 (m, 6H).

Scheme I-38 MS(ESI) (m/z): 420 (M+H)⁺. ¹H NMR (400 MHz, DMSO-d₆) δ 10.08 (s, 1H), 7.62-7.44 (m, 3H), 7.24 (d, J=8.5 Hz, 2H), 6.88 (d, J=7.8 Hz, 1H), 5.33 (s, 2H), 3.37 (s, 4H), 3.04 (s, 2H), 2.30 (s, 4H).

Application Case 12: Synthesis of 4-((2-phenylpyridin-4-yl)methoxy)-N-(pyridin-3-yl)benzo[d]isoxazol-3-amine (Scheme I-39)

1. Synthesis of 2-phenylisonicotinaldehyde (compound 34)

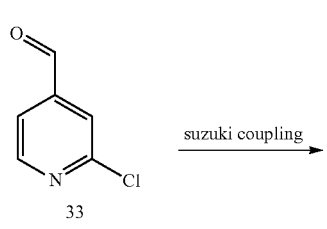

Dissolve 500 mg 2-chloroisonicotinaldehyde (3.53 mmol, 1.0 eq) and 517 mg phenylboronic acid (4.24 mmol, 1.2 eq) in 50 mL toluene, add 204 mg tetrakis(triphenylphosphine) palladium (0.177 mmol), 0.05 eq) and 2N sodium carbonate (3.53 mL), heated to 90° C. for 12 h under nitrogen, add water, extracted with EA, the organic layers washed with saturated sodium chloride solution, dried over Na₂SO₄, filtered, and concentrated. The residue was purified with column chromatography (PE/EA=15:1) to give compound 34, 455 mg white solid, yield 70%.

The structure is confirmed correct and data are as follow: MS (ESI): m/z 184[M+H]⁺. ¹H NMR (400 MHz, DMSO-d₆) δ 10.14 (s, 1H), 8.93 (dd, J=4.9, 0.9 Hz, 1H), 8.39 (s, 1H), 8.17-8.12 (m, 2H), 7.74 (dd, J=4.9, 1.4 Hz, 1H), 7.56-7.45 (m, 3H).

2. Synthesis of (2-phenylpyridin-4-yl)methanol (Compound 35)

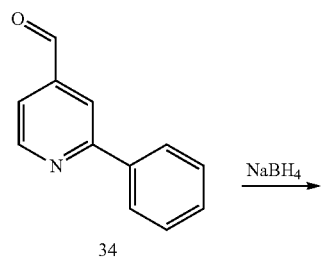

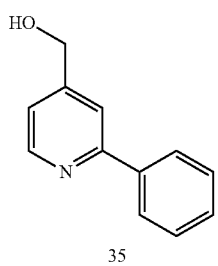

Referring to the synthesis of compound 14.

The structure is confirmed correct and data are as follow: MS (ESI): m/z 186[M+H]⁺. ¹H NMR (400 MHz, DMSO-d₆) δ 8.57 (dd, J=5.0, 0.8 Hz, 1H), 8.08-8.01 (m, 2H), 7.85 (dd, J=1.6, 0.8 Hz, 1H), 7.52-7.44 (m, 2H), 7.43-7.38 (m, 1H), 7.30-7.26 (m, 1H), 5.49 (t, J=5.8 Hz, 1H), 4.60 (dt, J=5.8, 0.9 Hz, 2H).

3. Synthesis of 4-((2-phenylpyridin-4-yl)methoxy)-N-(pyridin-3-yl)benzo[d]isoxazol-3-amine (Scheme I-39)

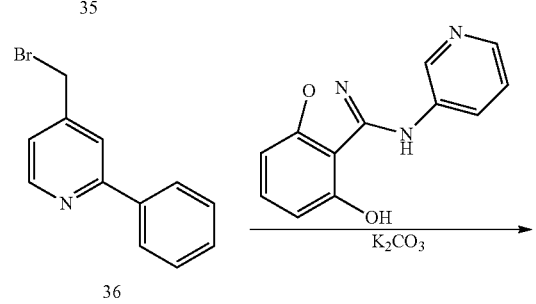

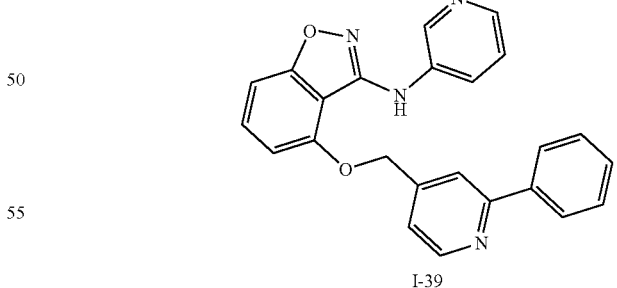

According to the conditions of the fifth and six-step synthesis of the Scheme I-1 in application case 1, the substituted benzyl alcohol was used to prepare substituted benzyl bromide, followed by 3-(Pyridin-3-ylamino)benzo[d]isoxazol-4-ol reaction to obtain the corresponding target compound I-39.

The structure is confirmed correct and data are as follow: Scheme I-39 MS(ESI) (m/z): 395 (M+H)⁺. ¹H NMR (400

MHz, DMSO-d$_6$) δ 8.85 (d, J=2.8 Hz, 1H), 8.66 (d, J=5.0 Hz, 1H), 8.53 (s, 1H), 8.19 (dd, J=4.7, 1.4 Hz, 1H), 8.16 (s, 1H), 8.10 (dd, J=8.4, 2.8 Hz, 1H), 8.08-8.03 (m, 2H), 7.52 (d, J=8.2 Hz, 1H), 7.50-7.41 (m, 4H), 7.38-7.33 (m, 1H), 7.17 (d, J=8.4 Hz, 1H), 6.87 (d, J=8.0 Hz, 1H), 5.55 (s, 2H).

Application Case 13: Synthesis of Tert-Butyl 4-(3-((3-(pyridin-3-ylamino)benzo[d]isoxazol-4-yl)oxy)propyl)piperidine-1-carboxylate (Scheme I-40)

1. Synthesis of Tert-Butyl 4-(3-((methylsulfonyl)oxy)propyl)piperidine-1-carboxylate (Compound 38)

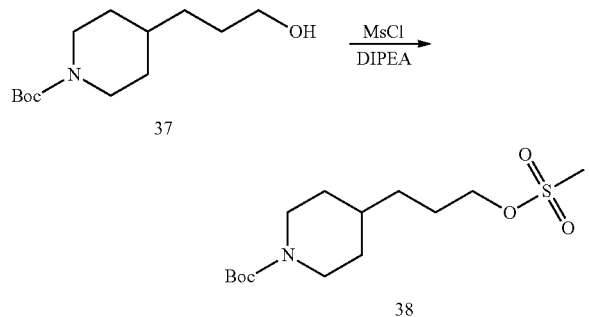

Dissolve 250 mg compound 37 (1.03 mmol, 1.0 eq) and 159 mg DIPEA (diisopropylethylamine) (1.23 mmol, 1.2 eq) in 5 mL dry DCM. Then 1.44 mg methanesulfonyl chloride (1.23 mmol, 1.2 eq) was added dropwise in the system under ice-water bath, and the reaction was carried out in an ice water bath for 15 min, then raised to room temperature and reacted overnight. Add water, extracted with DCM, the organic layers washed with saturated sodium chloride solution, dried over Na$_2$SO$_4$, filtered, and concentrated. It was used in the next reaction without further purification.

2. Synthesis of Tert-Butyl 4-(3-((3-(pyridin-3-ylamino)benzo[d]isoxazol-4-yl)oxy)propyl)piperidine-1-carboxylate (Scheme I-40)

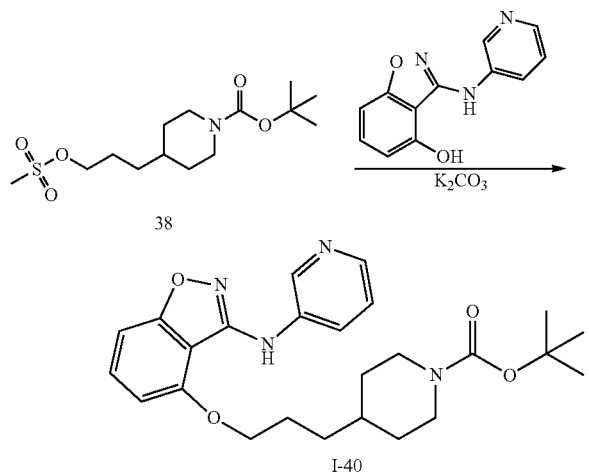

Referring to the conditions for synthesizing scheme I-1 in the sixth step in application case 1, compound 38 was substituted for substituted benzyl bromide to react with 3-(Pyridin-3-ylamino)benzo[d]isoxazol-4-ol to obtain the corresponding target compound I-40.

The structure is confirmed correct and data are as follow: Scheme I-40 MS(ESI) (m/z): 453 (M+H)$^+$. $^1$H NMR (400 MHz, DMSO-d$_6$) δ 8.80 (t, J=3.3 Hz, 1H), 8.22 (ddt, J=6.2, 3.3, 1.5 Hz, 2H), 8.09 (ddt, J=8.3, 3.0, 1.7 Hz, 1H), 7.55 (t, J=8.1 Hz, 1H), 7.41 (dd, J=8.3, 4.7 Hz, 1H), 7.17 (dd, J=8.3, 6.4 Hz, 1H), 6.88 (t, J=7.1 Hz, 1H), 4.23 (t, J=6.4 Hz, 2H), 3.92 (s, 2H), 2.67 (s, 2H), 1.92 (d, J=7.6 Hz, 2H), 1.67 (d, J=12.9 Hz, 2H), 1.44 (d, J=29.6 Hz, 3H), 1.38 (s, 9H), 0.99 (dd, J=15.0, 10.4 Hz, 2H).

Application Case 14: Preparation of Hydrochloride Salt of Scheme I-2

Dissolve 0.60 g compound I-2 (1.63 mmol, 1.0 eq) in 10 mL anhydrous ethyl acetate, and add 1.44 mL HCl (g) (1.8 mmol, 1.1 eq) in ethyl acetate (c=1.25 mol/L) to the above solution dropwise under ice-water bath, suction filtered after 10 minutes of reaction, and dried to obtain 0.53 g of white powdery solid in 80% yield.

Application Case 15: Determination of In Vitro Inhibition of Alkoxybenzeno Five- or Six-Member Heterocyclic Amines to Sphingomyelin Synthase 2

Laboratory Instruments and Materials
1. Electric-heated thermostatic water bath (Shanghai Hengyi Science and Technology Co., Ltd.)
2. Vortex Mixers (XW-80A, Shanghai Jingke Industrial Co., Ltd.)
3. High-speed centrifuge (Eppendorf 5804R)
4. HPLC Agilent 1100 (Agilent Technologies, Palo Alto, Calif., USA), equipped with a quaternary pump, a vacuum degassing and an FLD fluorescence detector.
5. HPLC Column: COSMOSIL 5C18-MS-II (4.6 mm I.D.× 250 mm).
6. DMPC. Purchased from Santa Cruz (USA) and dissolved in ethanol to prepare a solution of 40 mmol/L.
7. C6-NBD-Ceramide (6-((N-(7-nitrobenz-2-oxa-1,3-diazol-4-yl)amino)hexanoyl)-sphingosine). Purchased from Santa Cruz (USA) and dissolved in DMSO to prepare a solution of 1.16 mmol/L.
8. The organic solvents were purchased from Shanghai Sinopharm Reagent Company; methanol is of HPLC grade; water is ultrapure water filtrated by Milli-Q pump and deionized and ultrafiltrated by 0.22 μm ultrafiltration membrane. Other biological supplies are purchased in domestic companies.
9. Preparation of under tested compound solution: To each accurate weighed compound for 1~2 mg, an appropriate amount of DMSO was added to formulate a stock solution of 3 mmol/L precisely. To a certain volume of the DMSO stock solution of the test compound, the appropriate volume of DMSO was added to dilute the solution to the desired concentration.
10. SMS1, SMS2 pure enzyme DDM solution and buffer were provided by Yu, Cao research group of National Protein Science Center (Shanghai).

Part 1. Activity Assay for Inhibition of Alkoxybenzeno Five- or Six-Member Heterocyclic Amines to Sphingomyelin Synthase 2

Add 0.03 μL SMS2 pure enzyme DDM solution (total protein content 1.5 μg/μL), 1 μL test compound in DMSO solution or blank DMSO solution, 79.7 μL DDM buffer to 1.5 mL Eppendorf tube, vortex 30 seconds, let stand at room temperature for 5 min. Then add 20 μL DDM buffer containing 1 μL DMPC in ethanol (40 mmol/L) and 1 μL C6-NBD-Ceramide in DMSO (1.16 mmol/L). After vortexing for 30 seconds, Incubate for 0.5 h under water bath at 37° C. Then remove, add 200 μL of absolute ethanol, and vortex for 30 seconds. Take out 200 μL of the mixture and store it at 4° C. for high performance liquid chromatography analysis.

Part 2. Activity Assay for Inhibition of Alkoxybenzeno Five- or Six-Member Heterocyclic Amines to Sphingomyelin Synthase 1

Referring to the above SMS2 inhibitory activity detection method, and using SMS1 pure enzyme instead of SMS2 pure enzyme for corresponding operation.

Using the same HPLC fluorogenic quantitative detecting method as reference (Xiaodong Deng; Hong Sun; et al. *Analytical Letters*, 2012, 45:12, 1581-1589) to analyses samples obtained above. Analyze and record peak areas of C6-NBD-SM (Asm) and C6-NBD-Ceramide (Acer) of each sample from blank group, positive control group (compound D2) and under tested compound group. Calculate inhibition rate from the formula below:

$$\text{Inhibition rate }\% = \frac{\text{Blank}(Asm) - \text{Tested compound}(Asm)}{\text{Blank}(Asm)} \times 100$$

In vitro SMS2 inhibitory activity data of scheme I-1 I-38 obtained by HPLC fluorogenic quantitative detecting method are listed below:

Part 3. Determination of SMS2 Median Inhibitory Concentration (IC50) of Alkoxybenzeno Five- or Six-Member Heterocyclic Amines (Scheme I-1~I-38)

The DMSO stock solution of under tested compound (6 mM) was diluted stepwise into five concentration gradient. 1 μL solution of each concentration was added into the trial system to prepare samples with the method mentioned in the first step of application case 15. The Asm values of the five concentration solution of tested compound were measured (compound D2 is a positive control), and the inhibition rate under the five concentration were calculated and fitted to obtain median inhibitory concentration ($IC_{50}$). Each compound was measured three parallel groups. SMS2 median inhibitory concentration and SMS1 single inhibitory concentration (50 μM) of Scheme I-1~I-38, and SMS1 median inhibitory concentration of some compounds are listed below in Table 1.

Part 4. Determination of SMS1 Median Inhibitory Concentration (IC50) and SMS1 Single Concentration (50 μM) Inhibitory Concentration of Alkoxybenzeno Five- or Six-Member Heterocyclic Amines (Scheme I-1~I-38)

The experiment can be carried out with the corresponding concentration according to the operation similar to the determination of the median inhibitory concentration (IC50) of SMS2.

TABLE 1

SMS2 Median Inhibitory Concentration and SMS1 Single Inhibitory Concentration (50 μM) of Scheme I-1~I-38

| Scheme | SMS2 $IC_{50}$ (μM) | SMS1 Inhibition (50 μM) | SMS1 $IC_{50}$ (μM) | Selectivity ratio |
|---|---|---|---|---|
| D2 | 20.9[b] | 26% | — | — |
| I-1 | 0.117 | 65% | 40 | 342 |
| I-2 | 0.102 | 44% | 55 | 539 |
| I-3 | 2.000 | 49% | — | — |
| I-4 | 0.660 | 6% | — | — |
| I-5 | 0.156 | 6% | — | — |
| I-6 | 1.521 | 7% | — | — |
| I-7 | 0.270 | 41% | 79 | 292 |
| I-8 | 0.094 | 44% | 79 | 840 |
| I-9 | >10 | 5% | — | — |
| I-10 | 0.498 | 41% | 70 | 140 |
| I-11 | 0.190 | 20% | — | — |
| I-12 | >10 | 5% | — | — |
| I-13 | 0.255 | 21% | — | — |
| I-14 | 0.486 | 25% | — | — |
| I-15 | >10 | 9% | — | — |
| I-16 | 0.239 | 49% | 48 | 201 |
| I-17 | 0.523 | 17% | — | — |
| I-18 | >10 | −5% | — | — |
| I-19 | 0.107 | 59% | 67 | 726 |
| I-20 | 1.270 | 30% | — | — |
| I-21 | >10 | 5% | — | — |
| I-22 | 4.139 | 4% | — | — |
| I-23 | 0.945 | 8% | — | — |
| I-24 | >10 | −18% | — | — |
| I-25 | 0.153 | 53% | 47 | 307 |
| I-26 | 0.079 | 25% | 70 | 886 |
| I-27 | 0.720 | 30% | — | — |
| I-28 | 10.000 | 29% | — | — |
| I-29 | 10.000 | −7% | — | — |
| I-30 | >10 | 1% | — | — |
| I-31 | 1.459 | 13% | — | — |
| I-32 | >10 | 18% | — | — |
| I-33 | 0.860 | 60% | — | — |
| I-34 | 10.000 | 3% | — | — |
| I-35 | >10 | 11% | — | — |
| I-36 | >10 | 9% | — | — |
| I-37 | >10 | 60% | — | — |
| I-38 | >10 | −1% | — | — |
| I-39 | 13 | −6% | — | — |
| I-40 | −8.3% | 9% | — | — |
| D2 | 56.2[a] | — | — | — |

"a" refers to reference value.
"b" refers to experimental value.
"—" refers to not tested.

What is claimed is:

1. Benzeno five member heterocyclic amine compounds represented by formula (I), and their pharmaceutically acceptable salts, wherein formula (I) is

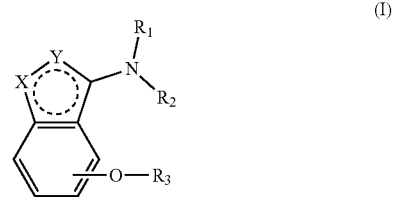

(I)

wherein,

X and Y are independently selected from oxygen, nitrogen, and sulfur; and X and Y are not both oxygen or sulfur;

$R_1$ is chosen from benzene ring or 5-6 membered heterocycle, wherein the heteroatoms in the heterocycle are one to three atoms optionally selected from oxygen, nitrogen and sulfur;

$R_2$ is chosen from one of hydrogen, methyl, ethyl, and propyl;

R₃ is chosen from phenyl methylene and substituted phenyl methylene, wherein the substituents in phenyl are one to three groups independently selected from halogen, —CN, $C_1$-$C_3$ alkyl, $C_1$-$C_3$ alkoxyl, $C_1$-$C_3$ haloalkyl, $C_1$-$C_3$ haloalkoxyl, wherein each of haloalkyl or haloalkoxyl independently contains one to three halogen atoms, the halogen atom is selected from F, Cl and Br, wherein the compounds comprise the following structures:

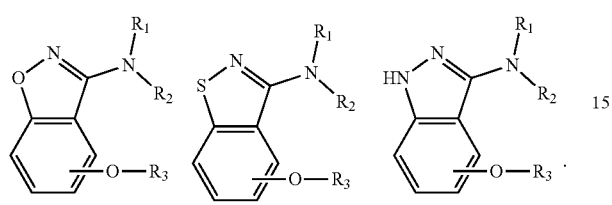

2. The heterocyclic amine compounds according to claim 1, further comprises the following structures:

Scheme I-1

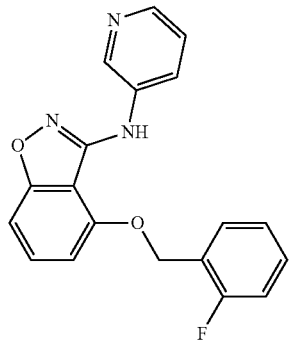

Scheme I-2

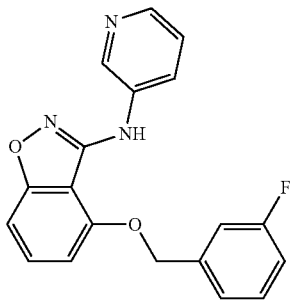

Scheme I-3

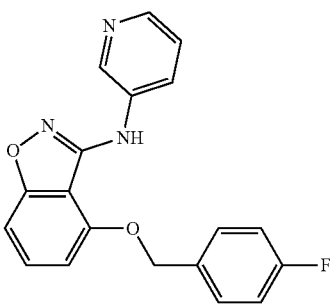

Scheme I-4

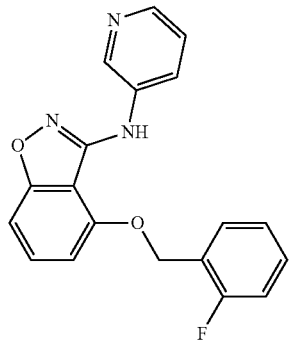

Scheme I-5

Scheme I-6

Scheme I-7

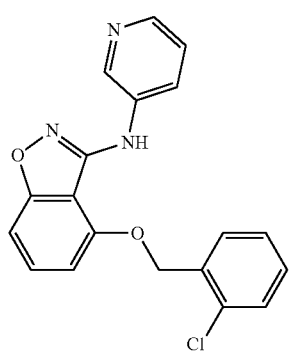

Scheme I-8

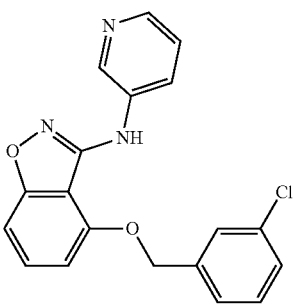

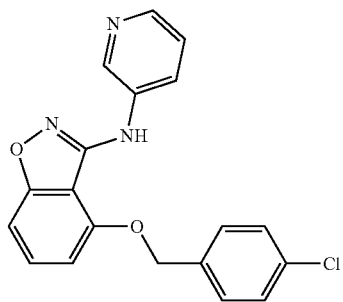
Scheme I-9
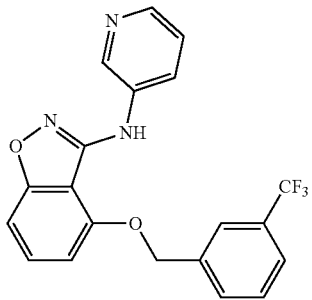
Scheme I-14
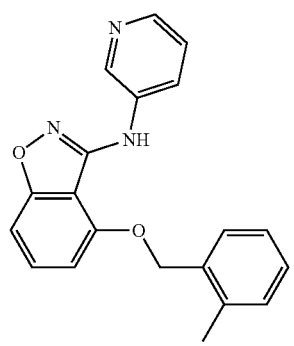
Scheme I-10
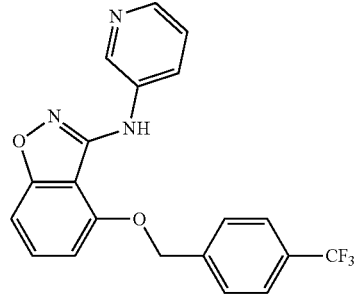
Scheme I-15
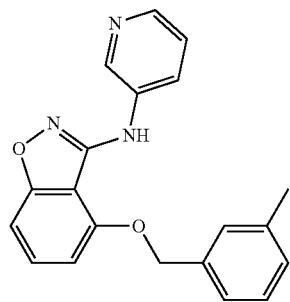
Scheme I-11
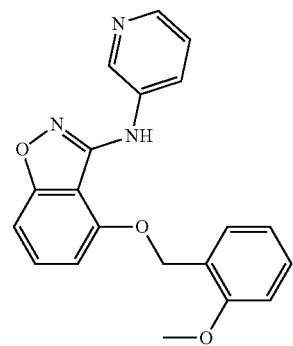
Scheme I-16
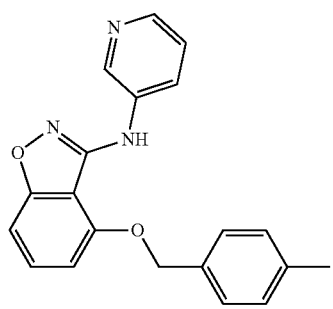
Scheme I-12
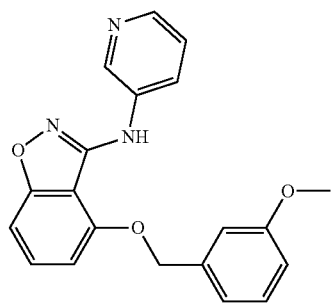
Scheme I-17
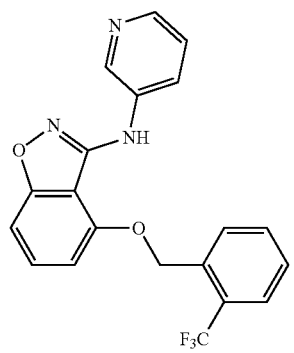
Scheme I-13
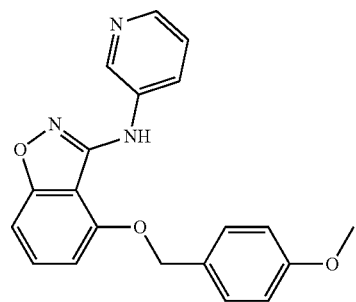
Scheme I-18

Scheme I-19
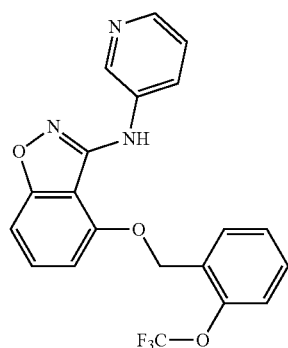
Scheme I-20
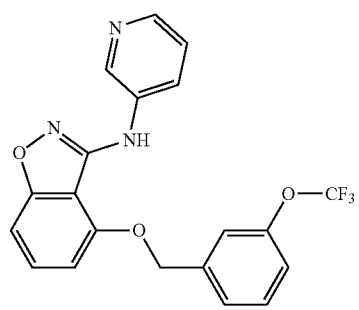
Scheme I-21
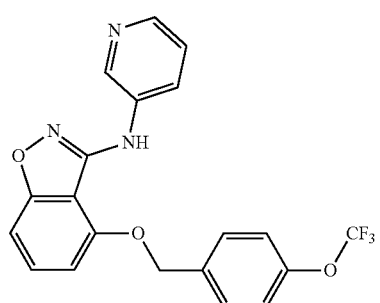
Scheme I-22
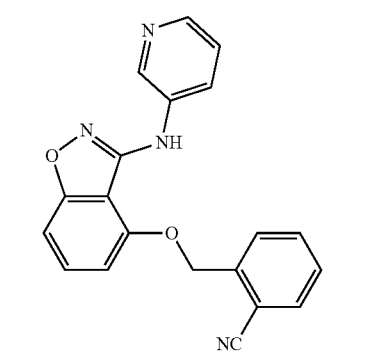
Scheme I-23
Scheme I-24
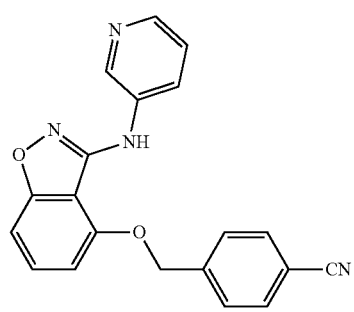
Scheme I-25
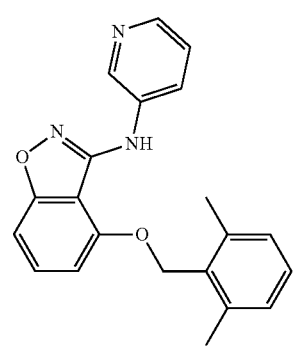
Scheme I-26
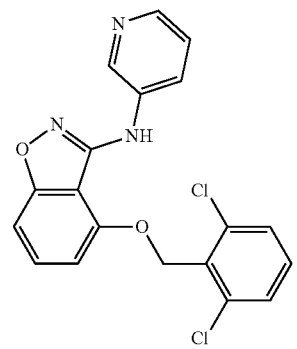
Scheme I-27
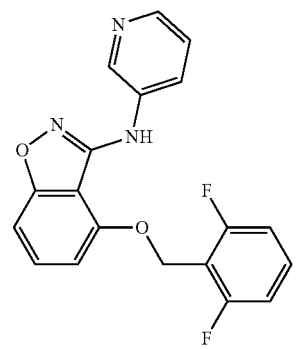

53
-continued

Scheme I-28
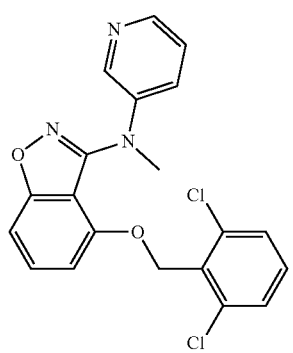

Scheme I-29
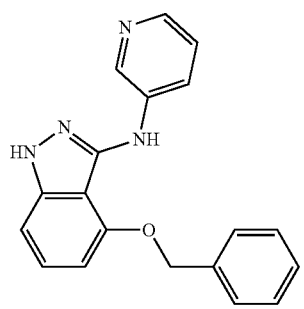

Scheme I-31
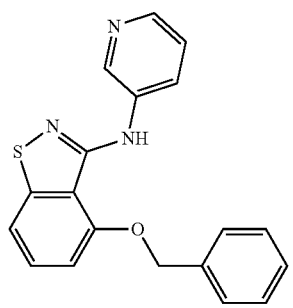

Scheme I-33
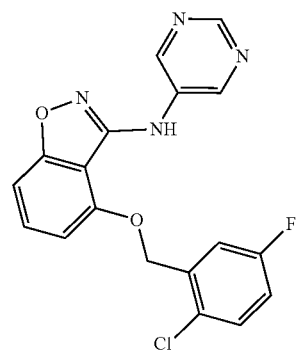

Scheme I-39
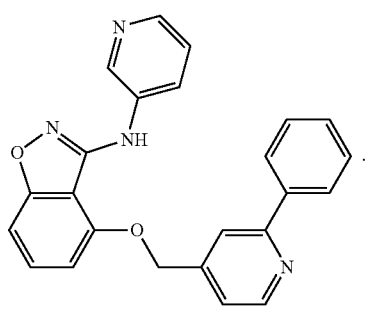

54

3. The heterocyclic amine compounds according to claim 1, wherein the pharmaceutically acceptable salts comprise hydrochloride salts, hydrogen bromide salts, tartrate and methanesulfonate.

4. A pharmaceutical composition with medicinally acceptable carriers comprising the heterocyclic amine compounds and their pharmaceutically acceptable salts according to claim 1.

5. A method of treatment of abnormal increase of sphingomyelin level, comprising treating a patient of said disease with the pharmaceutical composition with medicinally acceptable carriers, the heterocyclic amine compounds and their pharmaceutically acceptable salts according to claim 1.

6. The heterocyclic amine compounds according to claim 1, wherein the pharmaceutically acceptable salts comprise solvates of the heterocyclic amine compounds, wherein the solvates comprise water, ethanol, and methanol.

7. A method of treatment of diseases caused by abnormal increase of sphingomyelin level, comprising treating a patient of said diseases with drugs prepared from the pharmaceutical composition with medicinally acceptable carriers, the heterocyclic amine compounds and their pharmaceutically acceptable salts according to claim 5.

8. The method according to claim 7, wherein the diseases are selected from atherosclerosis, type II diabetes, fatty liver, obesity, metabolic syndromes, enteritis and other inflammatory diseases.

9. The heterocyclic amine compounds according to claim 1, wherein the compounds comprise the following structures:

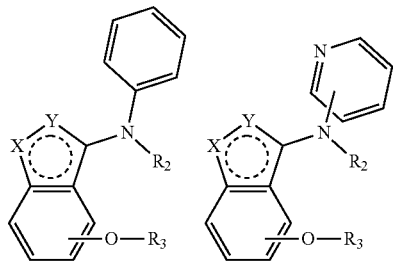

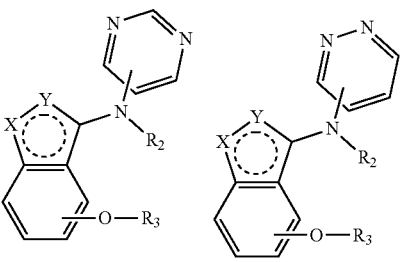

wherein X, Y, $R_2$ and $R_3$ are defined as above in claim 1.

10. The pharmaceutical composition with medicinally acceptable carriers comprising the heterocyclic amine compounds and their pharmaceutically acceptable salts according to claim 4, wherein the pharmaceutically acceptable salts comprise solvates of the heterocyclic amine compounds, wherein the solvates comprise water, ethanol, and methanol.

* * * * *